(12) United States Patent
Hou et al.

(10) Patent No.: US 12,383,655 B2
(45) Date of Patent: Aug. 12, 2025

(54) METHODS OF ISOLATING AND USING DESCEMET'S MEMBRANE AND COMPOSITIONS INCLUDING ISOLATED DESCEMET'S MEMBRANE

(71) Applicant: REGENTS OF THE UNIVERSITY OF MINNESOTA, Minneapolis, MN (US)

(72) Inventors: Joshua Honghan Hou, Minneapolis, MN (US); Peter Bedard, St. Paul, MN (US); Ching Yuan, St. Paul, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 936 days.

(21) Appl. No.: 17/286,537

(22) PCT Filed: Oct. 18, 2019

(86) PCT No.: PCT/US2019/056938
§ 371 (c)(1),
(2) Date: Apr. 19, 2021

(87) PCT Pub. No.: WO2020/081934
PCT Pub. Date: Apr. 23, 2020

(65) Prior Publication Data
US 2021/0379246 A1    Dec. 9, 2021

Related U.S. Application Data

(60) Provisional application No. 62/747,715, filed on Oct. 19, 2018.

(51) Int. Cl.
*A61L 27/36* (2006.01)
*A61L 27/38* (2006.01)
*C12N 5/0797* (2010.01)

(52) U.S. Cl.
CPC ....... *A61L 27/3675* (2013.01); *A61L 27/3604* (2013.01); *A61L 27/3683* (2013.01);
(Continued)

(58) Field of Classification Search
None
See application file for complete search history.

(56) References Cited

U.S. PATENT DOCUMENTS 5,152,786 A    10/1992  Hanna
5,964,748 A    10/1999  Peyman
(Continued)

FOREIGN PATENT DOCUMENTS

CN    1635115 A    7/2005
CN    106955372 A  *  7/2017  ......... A61L 27/3633
(Continued)

OTHER PUBLICATIONS

Alexandra Mikhailova et al. "Human pluripotent stem cell-derived limbal epithelial stem cells on bioengineered matrices for corneal reconstruction." Experimental Eye Research, vol. 146 (2016) pp. 26-34. (Year: 2016).*

(Continued)

*Primary Examiner* — Isaac Shomer
(74) *Attorney, Agent, or Firm* — Mueting Raasch Group

(57) ABSTRACT

This disclosure describes methods of preparing a decellularized Descemet's membrane and an isolated Descemet's membrane, methods of using an isolated Descemet's membrane, and tissues prepared using an isolated Descemet's membrane. This disclosure further describes a composition that includes an isolated Descemet's membrane. In some embodiments, the tissues and methods described herein may be used to treat a limbal stem cell deficiency or as an ocular surface bandage.

25 Claims, 27 Drawing Sheets

(52) U.S. Cl.
CPC ........ *A61L 27/3834* (2013.01); *C12N 5/0623* (2013.01); *A61L 2430/16* (2013.01); *C12N 2533/90* (2013.01)

(56) References Cited

U.S. PATENT DOCUMENTS

| | | | |
|---|---|---|---|
| 7,347,876 | B2 | 3/2008 | Tsai |
| 7,723,287 | B1* | 5/2010 | Savion ............... A61K 38/1709 |
| | | | 514/134 |
| 8,889,415 | B2 | 11/2014 | Tsai |
| 10,041,865 | B2 | 8/2018 | Tran |
| 2003/0027333 | A1* | 2/2003 | De Luca .............. C12N 5/0621 |
| | | | 435/368 |
| 2003/0208266 | A1* | 11/2003 | Tsai ......................... A61F 2/02 |
| | | | 623/23.72 |
| 2010/0057093 | A1 | 3/2010 | Ide et al. |
| 2010/0256651 | A1 | 10/2010 | Jani et al. |
| 2011/0144579 | A1 | 6/2011 | Elton |
| 2014/0155871 | A1 | 6/2014 | Cumming |
| 2014/0171956 | A1 | 6/2014 | Helmy et al. |
| 2014/0180221 | A1 | 6/2014 | Dias et al. |
| 2018/0106704 | A1 | 4/2018 | Tran |
| 2018/0161149 | A1 | 6/2018 | Litvin |
| 2019/0343848 | A1* | 11/2019 | Rigas ...................... A61P 27/04 |
| 2020/0338235 | A1 | 10/2020 | Honghan et al. |
| 2022/0183818 | A1 | 6/2022 | Binner et al. |
| 2022/0400655 | A1 | 12/2022 | Hou et al. |

FOREIGN PATENT DOCUMENTS

| | | | |
|---|---|---|---|
| WO | WO 00/47040 | A1 | 8/2000 |
| WO | WO 2008/155748 | A2 | 12/2008 |
| WO | WO 2020/081934 | A1 | 4/2020 |
| WO | WO 2022/241252 | A1 | 11/2022 |

OTHER PUBLICATIONS

S. Elizabeth James et al. "The Potential for Eye Bank Limbal Rings to Generate Cultured Corneal Epithelial Allografts." Cornea, vol. 20(5), 2001, pp. 488-494. (Year: 2001).*

English Translation of CN- 106955372-A. Obtained by examiner on Feb. 2, 2024. Originally published in Chinese on Jul. 18, 2017, 7 printed pages. (Year: 2017).*

Kimberly A. Mace and Kristin M. Braun. "Progenitor Cells." Humana Press, 2012, pp. i-xiv and 1408. (Year: 2012).*

M Regnier, C Auxenfans, D Maucort-Boulch, A-S Marty, O DAmour, C Burillon, V Kocaba. "Eye bank prepared versus surgeon cut encothelial graft tissue for Descemet membrane endothelial keratoplasty." Medicine, vol. 96:19, 2017, pp. 1-7. (Year: 2017).*

DL DeMill, KD Tran, ZM Mayko, K Downes, CS Sales, MA Terry. "Frozen, Pre-stripped Descemet Membrane Endothelial Keratoplasty (DMEK) Grafts for Surgical Training." International Journal of Eye Banking, vol. 5 No. 2, Jul. 2017, pp. 1-7. (Year: 2017).*

Alvarez et al., Reformulation of Fungizone by PEG-DSPE Micelles: Deaggregation and Detoxification of Amphotericin B. *Pharm Res* 33, 2098-2106 (2016).

Atallah et al., Limbal stem cell transplantation: current perspectives. Clin Ophthalmol 10, 593-602 (2016).

Badv et al., An omniphobic lubricant-infused coating produced by chemical vapor deposition of hydrophobic organosilanes attenuates clotting on catheter surfaces. *Sci Rep* 7, 11639 (2017).

Bhogal et al., Real-time assessment of corneal endothelial cell damage following graft preparation and donor insertion for DMEK. PLoS One 12, e0184824 (2017).

Brennan, "DMEK: New Insights, Emerging Advances" Review of Ophthalmology, Nov. 9, 2018; [retrieved Oct. 21, 2023]. Retrieved from the Internet: <URL: www.reviewofophthalmology.com/article/dmek-new-insights-emerging-advances> 9 pages.

Brothers et al., Association Between Fungal Contamination and Eye Bank-Prepared Endothelial Keratoplasty Tissue: Temperature-Dependent Risk Factors and Antifungal Supplementation of Optisol-Gentamicin and Streptomycin. *JAMA Ophthalmol* 135, 1184-1190 (2017).

Casaroli-Marano et al., Potential Role of Induced Pluripotent Stem Cells (IPSCs) for Cell-Based Therapy of the Ocular Surface. J Clin Med 4, 318-342 (2015).

Chandradoss et al., Surface Passivation for Single-molecule Protein Studies. J. Vis. Exp. (86), e50549, doi:10.3791/50549 (2014).

Chen et al., A new isolation method of human limbal progenitor cells by maintaining close association with their niche cells. Tissue Eng Part C Methods 17, 537-548 (2011).

Chen et al., Surface modification of silicate glass using 3-(mercaptopropyl)trimethoxysilane for thiol-ene polymerization. Langmuir 27, 13754-13761 (2011).

Chen et al., Transplantation of adult human corneal endothelium ex vivo: a morphologic study. Cornea 20, 731-737 (2001).

Connon et al., The variation in transparency of amniotic membrane used in ocular surface regeneration. Br J Ophthalmol 94, 1057-61 (2010).

De Araujo et al., Corneal stem cells and tissue engineering: current advances and future perspectives, World J Stem Cells 7, 806-814 (2015).

Dirisamer et al., Efficacy of descemet membrane endothelial keratoplasty: clinical outcome of 200 consecutive cases after a learning curve of 25 cases. Arch Ophthalmol 129, 1435-1443 (2011).

Downes et al., Cumulative Endothelial Cell Loss in Descemet Membrane Endothelial Keratoplasty Grafts From Preparation Through Insertion With Glass Injectors. Cornea 37, 698-704 (2018).

Droutsas et al., Visual Outcomes After Descemet Membrane Endothelial Keratoplasty Versus Descemet Stripping Automated Endothelial Keratoplasty-Comparison of Specific Matched Pairs. Cornea 35, 765-771 (2016).

Duncan et al., The Effect of Light Exposure on the Efficacy and Safety of Amphotericin B in Corneal Storage Media. JAMA Ophthalmol 134, 432-436 (2016).

Dunne et al., Human decellularized adipose tissue scaffold as a model for breast cancer cell growth and drug treatments. Biomaterials 35, 4940-4949 (2014).

EBAA-CS AAO 2018—ocular surface DM final, Cornea and Eye Banking Forum 2018, Chicago, IL, Oct. 28, 2018, 26 pages.

Edelstein SL, DeMatteo J, Stoeger CG, Macsai MS, Wang CH. Report of the Eye Bank Association of America medical review subcommittee on adverse reactions reported from 2007 to 2014. Cornea 2016;35:917-926.

Feizi et al., DMEK lenticule preparation using an air dissection technique: central versus peripheral injection. Eur J Ophthalmol 26, 6-11 (2016).

Feng et al., Review of alternative carrier materials for ocular surface reconstruction. Curr Eye Res 39, 541-552 (2014).

Gkana et al., Anti-adhesion and Anti-biofilm Potential of Organosilane Nanoparticles against Foodborne Pathogens. Front Microbiol 8, 1295 (2017).

Gloeckner et al., Monitoring of cell viability and cell growth in a hollow-fiber bioreactor by use of the dye Alamar Blue. J Immunol Methods 252, 131-138 (2001).

Gutermuth et al., Descemet's Membrane Biomimetic Microtopography Differentiates Human Mesenchymal Stem Cells Into Corneal Endothelial-Like Cells. Cornea 38, 110-119 (2019).

Haagdorens et al., Limbal Stem Cell Deficiency: Current Treatment Options and Emerging Therapies. Stem Cells Int 2016, 9798374 (2016).

Hansen, Apr. 23, 2019, "Video: Small relaxing incisions may allow easier DMEK surgery", available online [retrieved Apr. 25, 2019], 2 pages.

Hariya et al., Transparent, resilient human amniotic membrane laminates for corneal transplantation. Biomaterials 101, 76-85 (2016).

Heinzelmann et al., Influence of donor characteristics on descemet membrane endothelial keratoplasty. Cornea 33, 644-648 (2014).

Holland, Management of Limbal Stem Cell Deficiency: A Historical Perspective, Past, Present, and Future. Cornea 34 Suppl 10, S9-15 (2015).

(56) References Cited

OTHER PUBLICATIONS

Hou et al., Ex vivo expansion of limbal stem cells using Descemet's Membrane as a culture substrate. Invest Ophthalmol Vis Sci 60, 4128 (2019). Abstract presented at the 2019 ARVO Annual Meeting, Vancouver, Canada, Apr. 28,-May 2, 2019.

Hou, Ex vivo expansion of limbal stem cells using Descemet's membrane as a culture substrate. E-poster presented at the 37th Congress of the European Society of Cataract and Refractive Surgeons (ESCRS), Sep. 14-18, 2019, Paris, France. 6 pages.

Hou, "Ex vivo expansion of limbal stem cells using Descemet's membrane as a culture substrate" Presented at the 12th International Symposium no New Ophthalmic Technology. Jinan, Shandong Province, China. Aug. 24, 2019; 23 pages.

International Preliminary Report on Patentability for International Patent Application No. PCT/US2019/056938, Apr. 29, 2021, 9 pages.

International Search Report and Written Opinion for International Patent Application No. PCT/US2019/056938, Feb. 11, 2020, 11 pages.

International Search Report and Written Opinion for International Patent Application No. PCT/US2022/029249, mailed Aug. 11, 2022, 9 pages.

Janissen et al., Optimized straight forward procedure for covalent surface immobilization of different biomolecules for single molecule applications. Colloids Surf B Biointerfaces 71, 200-207 (2009).

Kabosova et al., Compositional differences between infant and adult human corneal basement membranes. Invest Ophthalmol Vis Sci 48, 4989-4999 (2007).

Khutoryanskaya et al., Multilayered hydrogel coatings covalently-linked to glass surfaces showing a potential to mimic mucosal tissues. Soft Matter, 2010, 6, 551-557.

Larson et al., A new, simple, nonradioactive, nontoxic in vitro assay to monitor corneal endothelial cell viability. Invest Ophthalmol Vis Sci 38, 1929-1933 (1997).

Layer et al., Efficacy and safety of antifungal additives in Optisol-GS corneal storage medium. JAMA Ophthalmol 132, 832-837 (2014).

Lohmeier et al., Viability of Descemet Membrane Endothelial Keratoplasty Grafts Folded in the Eye Bank. Cornea 37, 1474-1477 (2018).

LVG Patient Ready DMEK Press release page [online]. Lions Vision Gift, Boston, MA, 2019 [retrieved Oct. 21, 2023]. Retrieved from the Internet: <http://visiongift.org/wp-content/uploads/2019/02/LVG_DMEK_UPDATE_090717.pdf>, 1 page.

Maier et al., Influence of the difficulty of graft unfolding and attachment on the outcome in Descemet membrane endothelial keratoplasty. Graefes Arch Clin Exp Ophthalmol 253, 895-900 (2015).

Materne et al., Organosilane Technology in Coating Applications: Review and Perspectives. Dow Corning Corporation, Midland, MI; Copyright 2006, 2012; 16 pages.

Mittal K. Silanes and Other Coupling Agents, vol. 5. Boca Raton, FL: CRC Press; 2009.

Modabber et al., The role of novel DMEK graft shapes in facilitating intraoperative unscrolling. Graefes Arch Clin Exp Ophthalmol 256, 2385-2390 (2018).

Mohanty et al., Fabrication of scalable and structured tissue engineering scaffolds using water dissolvable sacrificial 3D printed moulds. Mater Sci Eng C Mater Biol Appl 55, 569-578 (2015).

Newman et al., Preloaded Descemet Membrane Endothelial Keratoplasty Donor Tissue: Surgical Technique and Early Clinical Results. Cornea 37, 981-986 (2018).

Parekh et al., Preloaded Tissues for Descemet Membrane Endothelial Keratoplasty. Am J Ophthalmol 166, 120-125 (2016).

Parekh et al., Preservation of Preloaded DMEK Lenticules in Dextran and Non-Dextran-Based Organ Culture Medium. J Ophthalmol 2016, 5830835 (2016).

Parekh et al., Standardizing Descemet Membrane Endothelial Keratoplasty Graft Preparation Method in the Eye Bank-Experience of 527 Descemet Membrane Endothelial Keratoplasty Tissues. Cornea 36, 1458-1466 (2017).

Park et al., Keratoplasty in the United States: A 10-Year Review from 2005 through 2014. Ophthalmology 122, 2432-2442 (2015).

Perrot et al. "A New Nondestructive Cytometric Assay Based on Resazurin Metabolism and an Organ Culture Model for the Assessment of Corneal Viability" Cytometry Part A, 2003; 55A:7-14.

Price et al., Evolution of endothelial keratoplasty. Cornea 32 Suppl 1, S28-32 (2013).

Proulx et al., Transplantation of a tissue-engineered corneal endothelium reconstructed on a devitalized carrier in the feline model. Invest Ophthalmol Vis Sci 50, 2686-2694 (2009).

Rennier et al., The role of death-associated protein kinase (DAPK) in endothelial apoptosis under fluid shear stress. Life Sci 93, 194-200 (2013).

Romano et al., Comparison of preservation and transportation protocols for preloaded Descemet membrane endothelial keratoplasty. Br J Ophthalmol 102, 549-555 (2018).

Sabater et al., Amniotic membrane use for management of corneal limbal stem cell deficiency. Curr Opin Ophthalmol 28, 363-369 (2017).

Sarnicola et al., Cannula-Assisted Technique to Unfold Grafts in Descemet Membrane Endothelial Keratoplasty. Cornea 38, 275-279 (2019).

Schallhorn et al., Quantification and Patterns of Endothelial Cell Loss Due to Eye Bank Preparation and Injector Method in Descemet Membrane Endothelial Keratoplasty Tissues. Cornea 35, 377-382 (2016).

Shafiq et al., Decellularized human cornea for reconstructing the corneal epithelium and anterior stroma. Tissue Eng Part C Methods 18, 340-348 (2012).

Sharifi et al., Isolation, culture, characterization and optimization of human corneal stem cells. Biocell 34, 53-55 (2010).

Silanikove and Shapiro, "Combined Assays for Lactose and Galactose by Enzymatic Reactions," in Dietary Sugars: Chemistry, Analysis, Function and Effects. *Preedy* (Ed.) RSC Publishing, The Royal Society of Chemistry: Cambridge, UK; 2012. Cover page, publisher's page, and pp. 395-404.

Singh et al., Science and Art of Cell-Based Ocular Surface Regeneration. Int Rev Cell Mol Biol 319, 45-106 (2015).

Suri et al., Human Platelet Lysate as a Replacement for Fetal Bovine Serum in Limbal Stem Cell Therapy. Curr Eye Res 41, 1266-1273 (2016).

Szurman, "Descemet Membrane Endothelial Keratoplasty: The Innovative System for Treating Endothelial Corneal Diseases" Product Brochure. Geuder AG, Heidelberg, Germany, 2017, 12 pages.

Terry, Endothelial keratoplasty: history, current state, and future directions. Cornea 25, 873-878 (2006).

Tran et al., Evaluation and Quality Assessment of Prestripped, Preloaded Descemet Membrane Endothelial Keratoplasty Grafts. Cornea 36, 484-490 (2017).

Tran et al., Measuring Endothelial Cell Loss on DMEK Grafts After Transplantation in Human Cadaveric Whole Eyes: Description of the Technique and Pilot Study. Cornea 37, 1075-1080 (2018).

Tsai et al., From stem cell niche environments to engineering of corneal epithelium tissue. Jpn J Ophthalmol 58, 111-119 (2014).

Wolle et al., Quantitative Analysis of Endothelial Cell Loss in Preloaded Descemet Membrane Endothelial Keratoplasty Grafts. Cornea 36, 1295-1301 (2017).

Zeidenweber et al., Prestained and Preloaded DMEK Grafts: An Evaluation of Tissue Quality and Stain Retention. Cornea 36, 1402-1407 (2017).

Zhang et al., An Ultra-thin Amniotic Membrane as Carrier in Corneal Epithelium Tissue-Engineering. Sci Rep 6, 21021 (2016).

Zhang et al., Comparison of Explant and Enzyme Digestion Methods for Ex Vivo Isolation of Limbal Epithelial Progenitor Cells. Curr Eye Res 41, 318-325 (2016).

Zhao et al., Systematic review and meta-analysis on transplantation of ex vivo cultivated limbal epithelial stem cell on amniotic membrane in limbal stem cell deficiency. Cornea 34, 592-600 (2015).

(56) References Cited

OTHER PUBLICATIONS

Zhou et al., Noninvasive real-time monitoring by alamarBlue((R)) during in vitro culture of three-dimensional tissue-engineered bone constructs. Tissue Eng Part C Methods 19, 720-729 (2013).

Guindolet et al., "Storage of Porcine Cornea in an Innovative Bioreactor" Investigative Ophthalmology & Visual Science, Nov. 2017; 58(13): 5907-5917.

Demill, David L. et al., Frozen, Pre-stripped Descemet Membrane Endothellal Keratoplasty (DMEK) Grants for Surgical Training, International Journal of Eye Banking, vol. 5 No. 2 (Jul. 2017).†

Regnier, Marie et al. Eye Bank Prepared Versus Surgeon Out Endothelial Graft Tissue for Descemet Membrane Endothelial Keratoplasty, Journal of Medicine (2017).†

\* cited by examiner
† cited by third party

Confluent sheet of limbal stem cells on DM

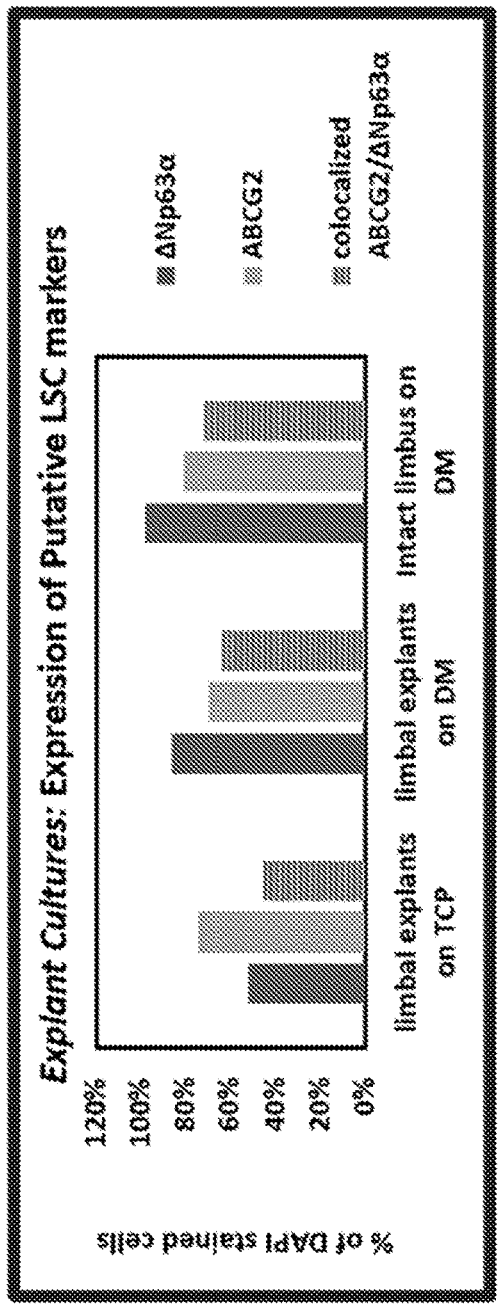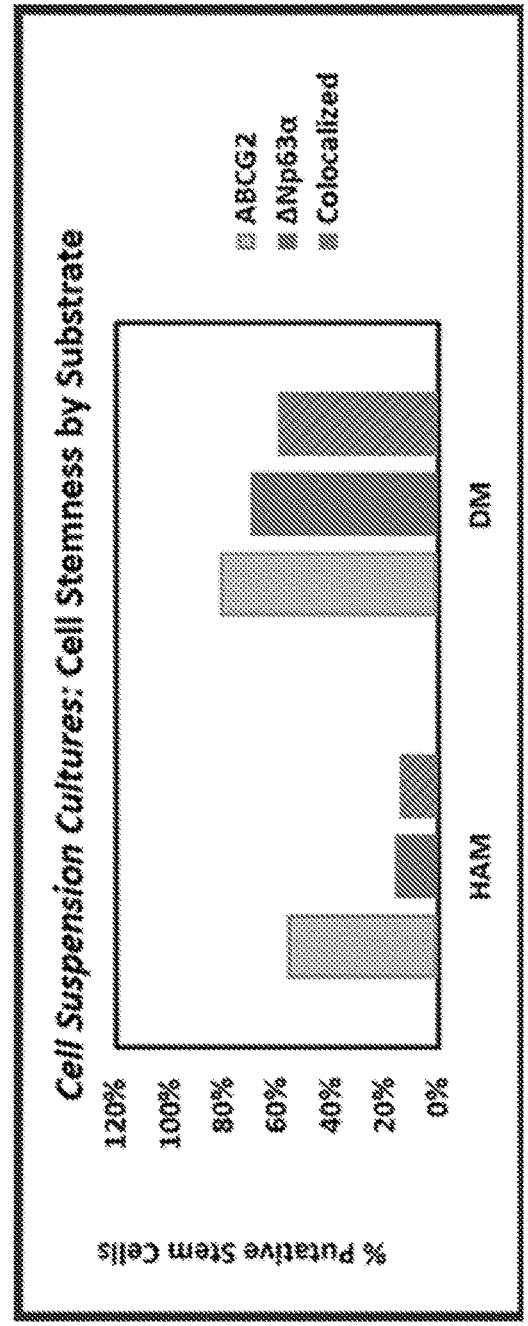

METHODS OF ISOLATING AND USING DESCEMET'S MEMBRANE AND COMPOSITIONS INCLUDING ISOLATED DESCEMET'S MEMBRANE

CONTINUING APPLICATION DATA

This application is the § 371 U.S. National Stage of International Application No. PCT/US2019/056938, filed Oct. 18, 2019, which claims the benefit of U.S. Provisional Application No. 62/747,715, filed Oct. 19, 2018, the disclosures of which are incorporated by reference herein in their entireties.

BACKGROUND

Limbal stem cell deficiency is a major cause of corneal blindness in the United States due to the limited treatment options available and poor long-term prognosis. Limbal stem cells are a population of pluripotent cells on the ocular surface that sustain and regenerate the vital, transparent epithelium of the cornea throughout life. In addition to being transparent, corneal epithelium is crucial for maintaining the avascularity of the cornea, protecting the cornea from infection, and maintaining a healthy tear film over the cornea. Loss of limbal stem cells due to chemical or thermal burns; iatrogenic trauma including, for example, overuse of contact lenses, chronic use of glaucoma drops, or ocular surgery; or an autoimmune disease including, for example, Steven Johnson Syndrome or ocular cicatricial pemphigoid, results in an inability to regenerate normal corneal epithelium on the ocular surface. This inability results in devastating pain and blindness due to corneal erosions, scarring, melting, and conjunctivalization.

SUMMARY OF THE INVENTION

This disclosure describes methods of preparing a decellularized Descemet's membrane and an isolated Descemet's membrane, methods of using an isolated Descemet's membrane, and tissues prepared using an isolated Descemet's membrane. This disclosure further describes a composition that includes an isolated Descemet's membrane. In some embodiments, the tissues and methods described herein may be used to treat a limbal stem cell deficiency or as an ocular surface bandage.

In one aspect, this disclosure provides a method that includes removing endothelium from a Descemet's membrane of a cornea to provide a decellularized Descemet's membrane and separating the decellularized Descemet's membrane from the stroma of the cornea to obtain an isolated Descemet's membrane.

In another aspect, this disclosure provides a composition that includes an isolated Descemet's membrane, wherein the Descemet's membrane has been decellularized and separated from the corneal stroma.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Reference throughout this specification to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout this specification are not necessarily referring to the same embodiment of the disclosure. Furthermore, the particular features, configurations, compositions, or characteristics may be combined in any suitable manner in one or more embodiments.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

All headings are for the convenience of the reader and should not be used to limit the meaning of the text that follows the heading, unless so specified.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

BRIEF DESCRIPTION OF THE FIGURES

FIG. 2A shows the forceful injection of air or fluid into the cornea, resulting in Descemet's membrane (DM) being separated from the stroma with an air or fluid bubble, as shown in FIG. 2B. Then, as shown in FIG. 2C, the stromal tissue may be excised, exposing the anterior DM to the corneolimbal ring. As shown in FIG. 2D, the corneolimbal ring with isolated DM attached 360° may be incubated in cell culture media, allowing limbal stem cells from the limbus to grow over the anterior surface of the DM, as shown in FIG. 2E. Finally, as shown in FIG. 2F, a confluent sheet of limbal stem cells on DM may be excised and transplanted onto an ocular surface. FIG. 2G shows a flow chart of some exemplary methods for making and using an isolated Descemet's membrane.

FIG. 3A shows a photograph of a donor cornea, with Descemet's membrane facing the camera. FIG. 3B shows a photograph of a donor cornea, with Descemet's membrane facing the camera, after fluid has been injected between the stroma of the cornea and Descemet's membrane has been separated from the corneal stroma by the fluid. FIG. 3C shows an optical coherence tomography (OCT) image of the injected fluid between the stroma of the cornea and isolated Descemet's membrane. FIG. 3D shows a photograph of a donor cornea mounted on a false anterior chamber. Descemet's membrane has already been separated from the corneal stroma by fluid and is facing away from the camera. In the photograph, the corneal stroma is being excised. FIG. 3E shows a photograph of a donor cornea after the stroma of the cornea has been removed, baring the anterior surface of Descemet's membrane, and exposing the Descemet's membrane to the corneolimbal ring, which contains the limbus and limbal stem cells. FIG. 3F shows a slit beam photograph of a donor cornea after the stroma of the cornea has been removed, and isolated Descemet's membrane has been bared, exposing the anterior surface of the isolated Descemet's membrane to the corneolimbal ring.

FIG. 4A shows Trypan blue staining of Descemet's membrane after limbal stem cells have grown onto Descemet's membrane from the intact corneolimbal ring. Trypan blue provides contrast to show where limbal stem cells have grown; Descemet's membrane that is not covered in limbal stem cells is stained blue, while Descemet's membrane that is covered in limbal stem cells remains clear. Most of the Descemet's membrane is covered in limbal stem cells. FIG. 4B shows immunofluorescence staining with Calcein AM; viable cells fluoresce green. The presence of green fluorescent cells covering Descemet's membrane demonstrates that viable cells are growing on Descemet's membrane. FIG. 4C shows a 10× image of immunofluorescence staining with Calcein AM. FIG. 4D shows a 4× phase contrast image. The cellular morphology of the cells on the Descemet's membrane is consistent with limbal stem cells. FIG. 4E shows a 10× phase contrast image. FIG. 4F shows red immunofluorescence staining for $\Delta Np63\alpha$, a stem cell marker expressed in cell nuclei, and green immunofluorescence staining for ABCG2, a stem cell marker expressed on cell membranes. Blue immunofluorescence staining for DAPI highlights all cell nuclei. The expression of both $\Delta Np63\alpha$ and ABCG2 in cells grown on the Descemet's membrane is consistent with a limbal stem cell phenotype.

FIG. 7A shows an unaltered donor cornea. FIG. 7B shows a donor cornea that has been cut with a microkeratome to remove the top 80% of the cornea to thin the cornea and reduce the total time needed to digest the cornea with collagenase. FIG. 7C shows complete digestion of the posterior 20% of the cornea and persistence of an intact Descemet's membrane after 45 minutes of exposure to collagenase A.

FIG. 12A shows limbal stem cells cultured from limbal explant fragments or from intact limbus on Descemet's membrane showed more co-localized expression of putative limbal stem cell markers (ABCG2 and $\Delta Np63\alpha$) than cells cultured on tissue culture plastic (TCP). FIG. 12B shows limbal stem cells seeded from suspension and cultured on Descemet's membrane showed more co-localized expression of putative limbal stem cell markers than cells seeded from suspension and cultured on human amniotic membrane (HAM).

DETAILED DESCRIPTION OF ILLUSTRATIVE EMBODIMENTS

Figure 1A:
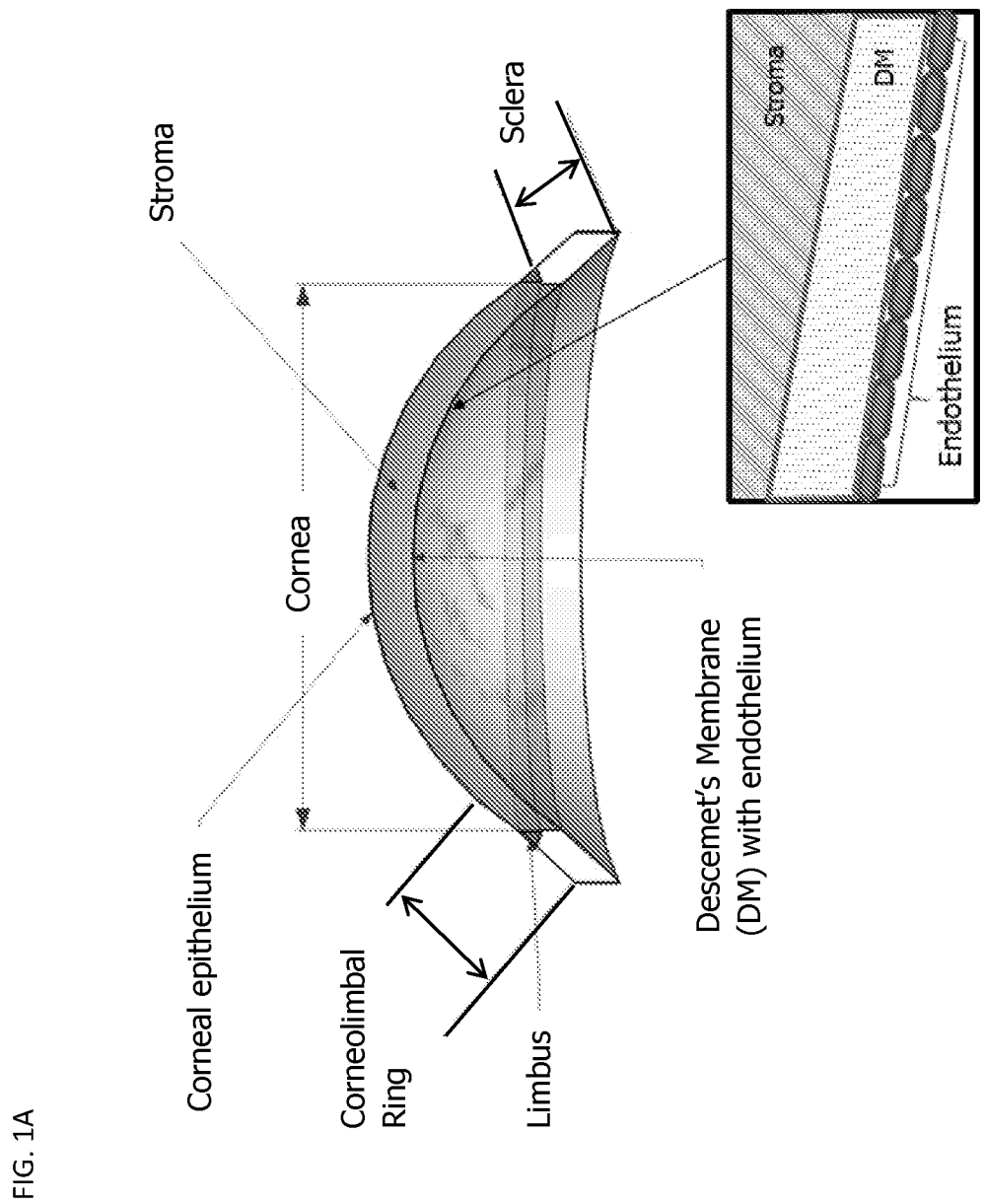
FIG. 1A shows a cross-sectional view of a cornea and FIG. 1B shows a frontal view of a cornea, indicating anatomical locations of the limbus on the anterior surface of the cornea. The corneolimbal ring includes the limbus and a small portion of the cornea and sclera immediately adjacent to the limbus. Descemet's membrane is located on the posterior surface of the cornea and, as shown in the inset to FIG. 1A, endothelium (also referred to herein as corneal endothelium) covers the posterior surface of Descemet's membrane.

This disclosure describes methods of preparing a decellularized Descemet's membrane and an isolated Descemet's membrane, methods of using an isolated Descemet's membrane, and tissues prepared using an isolated Descemet's membrane. This disclosure further describes a composition that includes an isolated Descemet's membrane. In some embodiments, the tissues and methods described herein may be used to treat a limbal stem cell deficiency or as an ocular surface bandage.

Existing Treatments for Limbal Stem Cell Deficiency

Several surgical options have been reported for the treatment of severe limbal stem cell deficiency: keratolimbal allografts (KLAL), simple limbal epithelial transplants (SLET), and cultured limbal transplants (CLET). The use of each of these techniques, as further described below, remains limited and suboptimal.

In KLAL the entire limbus and adjacent cornea and conjunctiva (corneolimbal ring) are excised from a donor cornea and the entire chunk of mixed tissues is transplanted on the recipient eye. This procedure results in a high rate of rejection because so many mixed tissues and antigens (including resident antigen-presenting dendritic cells in the limbus) are transplanted in addition to the limbal stem cells. Systemic immunosuppressive drugs must be administered to the patient to prevent rejection. Additionally, two donor corneas are usually required to have enough donor corneolimbal tissue to cover the damaged limbus of a single recipient eye. The procedure is also time-consuming and difficult for the surgeon because the dissection needs to be done in the operating room at the time of surgery (so that the graft is fresh). It can further be challenging to dissect out the donor limbus without injuring the donor stem cells or taking too much of the adjacent cornea and conjunctiva.

In SLET, a KLAL graft (corneolimbal ring) is harvested from a donor eye, but instead of being transplanted directly, the graft is cut into multiple small fragments (limbal explants). These explants are then scattered over the diseased cornea on a bed of amniotic membrane. Over time, limbal stem cells grow out from the fragments and resurface the cornea. The fragments are then removed after the cornea is covered with cells. Compared to KLAL, SLET does not require as much donor tissue and less extraneous tissue, aside from the limbal stem cells, is ultimately transplanted because the limbal fragments are removed. Nevertheless, results are still variable and suboptimal. The limbal fragments often dislodge before there is limbal stem cell outgrowth, resulting in a failed surgery. Also, significant trauma to the donor tissue may occur in preparing the explants, resulting in a significant portion of the fragments demonstrating no outgrowth of limbal stem cells. Prior to transplantation, there is also no way to objectively test the viability of the transplanted stem cells. Finally, the long-term survival of limbal stem cells on the cornea, outside of a limbal niche microenvironment, is limited. Without a limbal niche microenvironment, stem cells have difficulty maintaining their stem cell phenotype and often lose the ability to proliferate indefinitely.

One method of performing CLET is described in U.S. Pat. No. 7,347,876. Generally, in this method, limbal stem cells are removed from the intended recipient or a donor by taking small biopsies (explants) from the limbus of a healthy eye. The explants are then grown in culture on a human amniotic membrane. After a sheet of stem cells has been grown, the entire sheet, including the amniotic membrane, is transplanted onto a recipient eye. With this technique, a pure population of stem cells is transplanted, so the risk of immune rejection is presumed to be lower than with KLAL. Moreover, with CLET, a large number of stem cells may be transplanted from a small piece of donor limbus. Also, the viability of the stem cells in culture can be confirmed before transplantation surgery. Finally, with CLET, the bulk of the graft preparation work is done in the lab, outside of the operating room, saving surgeons time and money.

Several problems nevertheless exist with this method for preparing limbal stem cell grafts. The first is that using biopsies of limbal tissue results in significant trauma to the donor limbus and donor limbal stem cells. As a result, up to 20% of limbal explant cultures fail to grow in the lab. Second, using amniotic membrane introduces another potential exogenous source of infection to the transplant recipient because amniotic membrane is harvested from different donors than the donor used for the limbal biopsies. Therefore, additional risk of viral or bacterial transmission is introduced when using amniotic membrane. Third, though processed amniotic membrane has been shown to be non-immunogenic in most patients, additional antigens from the allogenic placental tissue may still be a risk factor in immune rejection of the transplanted graft. Fourth, the use of amniotic membrane as a substrate for the cell cultures requires a lot of resources; most surgeons do not have access to amniotic membrane-based CLET grafts. Moreover, amniotic membrane is expensive and difficult to store (requiring storage at −80° C. with a limited shelf life). Fifth, amniotic membrane is neither transparent nor perfectly stable on the ocular surface.

Because amniotic membrane is neither transparent nor completely stable on the ocular surface, there are two potential outcomes that occur after an amniotic membrane-based limbal stem cell graft is transplanted on the eye, and neither is ideal. One potential outcome is that the amniotic membrane persists and becomes incorporated on the cornea long-term. The clarity of the patient's cornea is compromised by the semi-opaque amniotic membrane, and vision can remain poor despite successful transplantation of viable limbal stem cells. The alternative outcome is that the amniotic membrane dissolves before becoming fully incorporated into the cornea. In this case, the cornea can be clear, but the transplanted stem cells lose the substrate that helps to sustain their viability and, potentially, their stem cell phenotype. Without a limbal niche microenvironment, it is very difficult for stem cells to maintain their stem cell phenotype. Stem cells growing directly on the cornea itself, outside a normal limbal niche microenvironment or limbal niche-like environment, will eventually differentiate into mature corneal epithelial cells and lose their ability to proliferate indefinitely. This differentiation results in long-term failure of the limbal stem cell transplants as terminally differentiated epithelial cells cannot sustain the ocular surface throughout the patient's lifetime. Consequently, long-term success (for example, beyond five years) remains limited with current amniotic membrane-based limbal stem cell grafts.

Figure 1B:
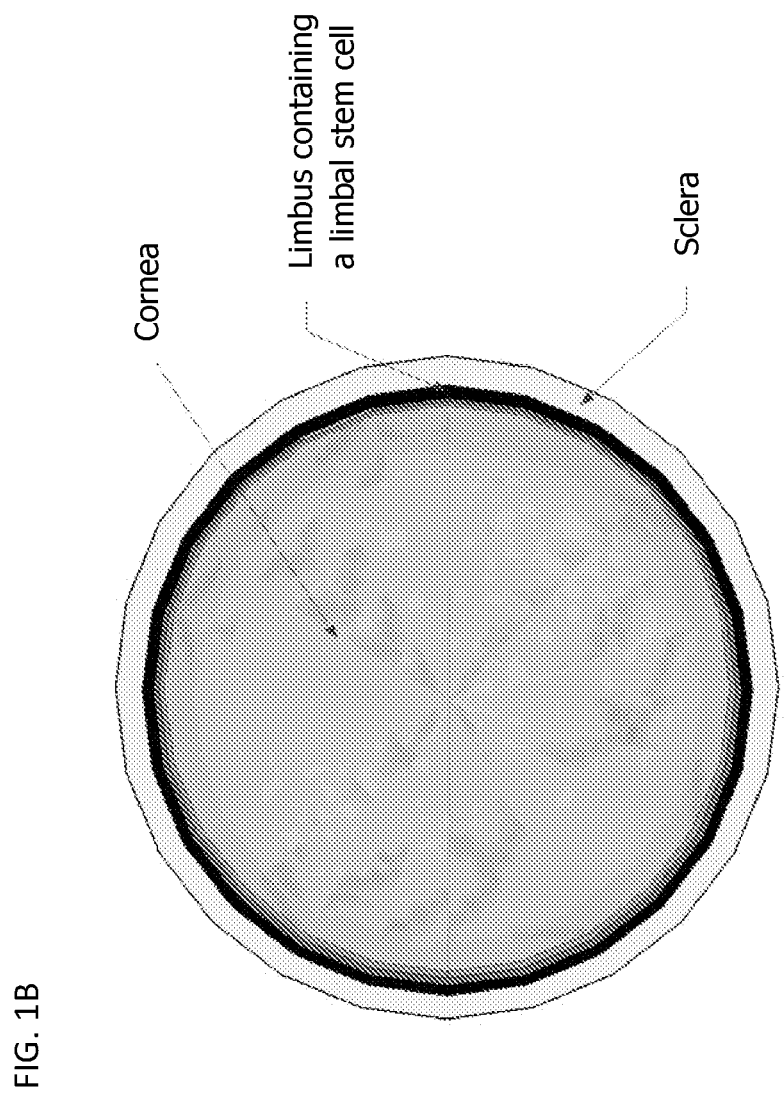

As further described herein, in some aspects, this disclosure describes a modified CLET that uses Descemet's membrane as a substrate for culturing limbal stem cells instead of amniotic membrane. Descemet's membrane is the multilayered basement membrane of the corneal endothelium (see FIG. 1). Descemet's membrane is routinely isolated, along with the endothelial cells, from donor corneas and transplanted intraocularly in patients to replaced damaged Descemet's membrane and/or corneal endothelial cells as reported by Park, et al., *Ophthalmology.* 2015; 122:2432-2442 (see also U.S. Pat. No. 8,889,415). Transplantation of Descemet's membrane onto the external ocular surface of the eye is not known to have been previously described.

As further described herein, Descemet's membrane unexpectedly provides multiple advantages as a substrate for supporting proliferation and long-term survival of limbal stem cells, both in vivo on the ocular surface and ex vivo in culture. The similarity of Descemet's membrane to the basement membrane of the limbal niche microenvironment, biochemically, is an obscure characteristic of Descemet's membrane that has not previously been exploited to promote the growth of limbal stem cells and to inhibit further differentiation into non-amplifying corneal epithelial cells. The methods of this disclosure exploit this characteristic of Descemet's membrane, and this disclosure describes, in some embodiments, a method of using Descemet's membrane as a substrate for culturing limbal stem cells.

Methods of Preparing Decellularized Descemet's Membrane and Isolated Descemet's Membrane In one aspect, this disclosure describes a method of removing endothelium from a Descemet's membrane of a cornea to provide a decellularized Descemet's membrane. In a further aspect, this disclosure describes separating a decellularized Descemet's membrane from the stroma of the cornea to obtain an isolated Descemet's membrane.

In some embodiments, the cornea may be a donor cornea including, for example, a cadaveric cornea. In some embodiments, the cornea may be a human cornea. In some embodiments, the cornea may be a porcine cornea.

In some embodiments, corneal endothelium may be separated from Descemet's membrane to form a decellularized Descemet's membrane using mechanical, enzymatic, and/or chemical decellularization. In some embodiments, the separation of the corneal endothelium from Descemet's membrane to form a decellularized Descemet's membrane leaves the corneal epithelium intact.

In some embodiments, a decellularized Descemet's membrane may be separated from the stroma of a cornea to obtain an isolated Descemet's membrane by manually peeling the Descemet's membrane from the stroma of the cornea. In some embodiments, the corneal epithelium may preferably be removed with the stroma of the cornea.

In some embodiments, a decellularized Descemet's membrane may be separated from the stroma of a cornea to obtain an isolated Descemet's membrane by injecting air or fluid or both into the cornea. The fluid may include any suitable fluid. In some embodiments, the fluid may include, for example, saline, corneal storage solution, or any buffered solution. In some embodiments, the residual cornea (e.g., including the corneal epithelium and corneal stroma) that has been separated from Descemet's membrane may be excised to expose the isolated Descemet's membrane.

Figure 2A:
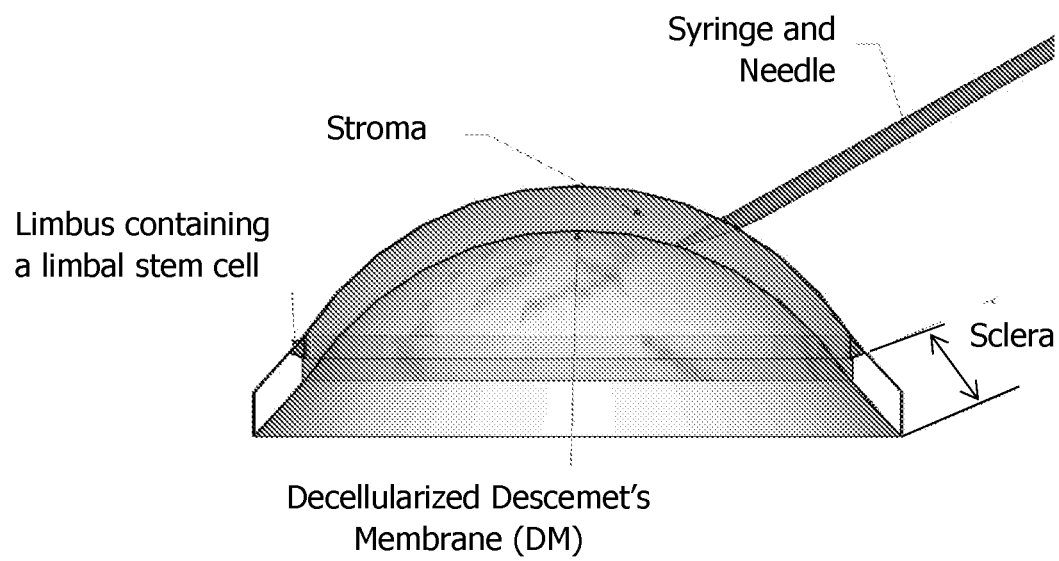
FIG. 2A-FIG. 2G show an exemplary method for the separation of a Descemet's membrane from the stroma of a cornea, and an exemplary method for using the isolated Descemet's membrane as a cell culture substrate for cultivating limbal stem cells and as a carrier for transplanting limbal stem cells.
Figure 2B:
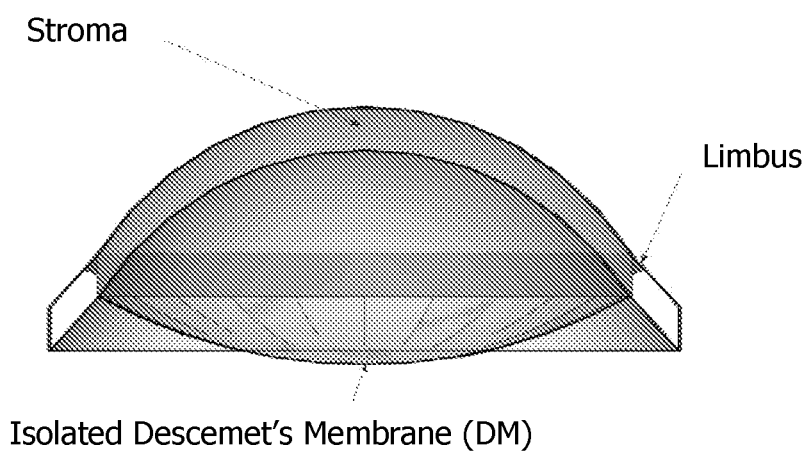
Figure 2C:
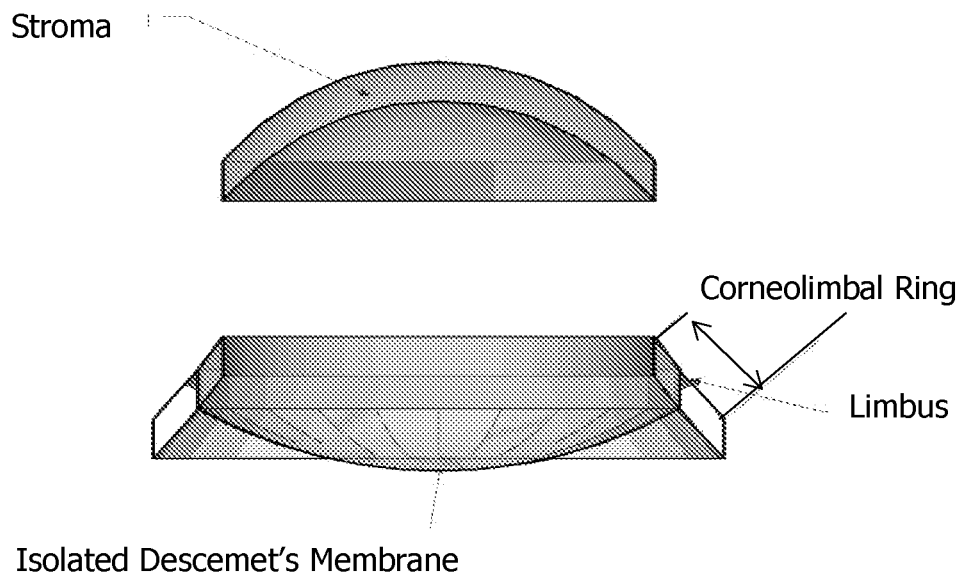

In some embodiments, separating the decellularized Descemet's membrane from the stroma of the cornea and removing that stroma includes exposing the isolated Descemet's membrane to a limbal stem cell found in the corneolimbal ring of the cornea. In some embodiments, the method may further include making a partial-thickness incision in the corneolimbal ring. Such an incision may promote the outgrowth of limbal stem cells from the corneolimbal ring. Drawings of one exemplary method of separating the decellularized Descemet's membrane from the stroma of the cornea and exposing the isolated Descemet's membrane to a limbal stem cell is shown in FIG. 2A-FIG. 2C.

In other embodiments, the isolated Descemet's membrane may be excised completely from the rest of the cornea (including the corneolimbal ring) including, for example, by trephinating the Descemet's membrane.

Methods of Storing an Isolated Descemet's Membrane

In another aspect, this disclosure describes a method of storing an isolated Descemet's membrane. In some embodiments, including, for example, when the Descemet's membrane has been completely excised by trephination or manually peeled from the rest of the cornea, the isolated Descemet's membrane may be preserved without regard to cell viability. In some embodiments, including, for example, when Descemet's membrane has not been completely excised from the corneolimbal ring or when the isolated Descemet's membrane has been used as a cell culture substrate, the isolated Descemet's membrane may be preserved by a means that maintains cell viability. In some embodiments, the isolated Descemet's membrane may be frozen, lyophilized, and/or cryopreserved.

In some embodiments, the isolated Descemet's membrane may be sterilized before or after preservation or both before and after preservation. The isolated Descemet's membrane may be sterilized by any suitable means including, for example, by gamma irradiation, chemical disinfectant, antibiotic treatment, ethylene oxide gas treatment, or supercritical $CO_2$ exposure.

Methods of Using an Isolated Descemet's Membrane

In a further aspect, this disclosure describes methods of using an isolated Descemet's membrane.

Methods of Using an Isolated Descemet's Membrane as a Cell Culture Substrate

In some aspects, this disclosure describes using an isolated Descemet's membrane as a cell culture substrate. For example, in some embodiments, this disclosure describes using an isolated Descemet's membrane as a cell culture substrate to support proliferation of a limbal stem cell. In some embodiments, the limbal stem cell may adhere to the isolated Descemet's membrane.

Figure 2D:
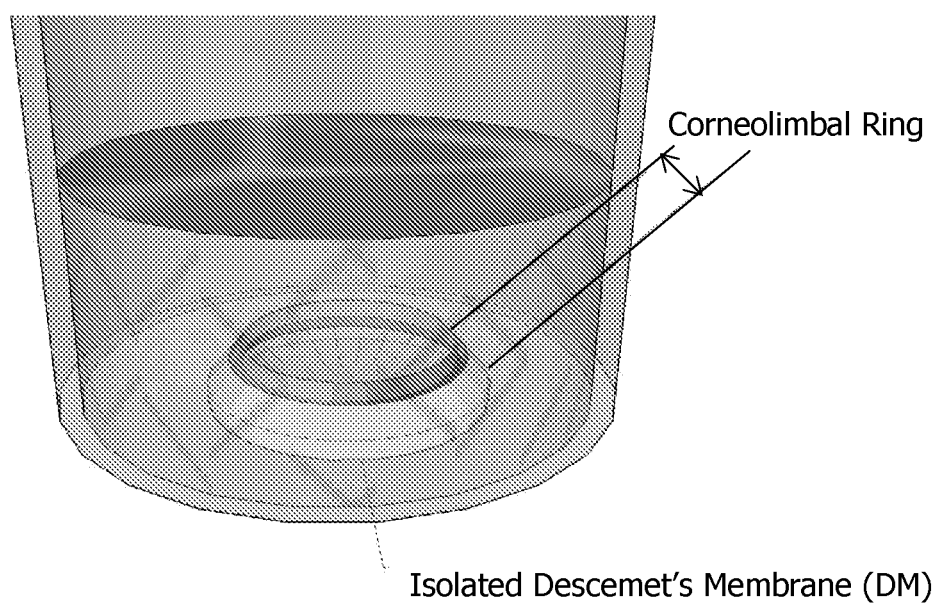

In some embodiments, an isolated Descemet's membrane may be attached to a cell culture surface including, for example, tissue culture plastic. A drawing of one exemplary method of attaching Descemet's membrane to a cell culture surface is shown in FIG. 2D. In some embodiments, the Descemet's membrane may be reversibly attached to the cell culture surface.

In some embodiments when an isolated Descemet's membrane is attached to a cell culture surface, the isolated Descemet's membrane will preferably have been completely excised or manually peeled from the rest of the cornea (including the corneolimbal ring). In some embodiments, including, for example, when an isolated Descemet's membrane is reversibly attached to a cell culture surface, a limbal explant may be cultured in the presence of the isolated Descemet's membrane. In some embodiments, the limbal explant may be from the same donor (for example, from the same cadaveric cornea) or different donor (for example, from a living donor's cornea) as the isolated Descemet's membrane. In some embodiments, the limbal explant includes a part of the corneolimbal ring. In some embodiments, the limbal explant includes an entire corneolimbal ring. In some embodiments, the limbal explant may be cultured under conditions that allow outgrowth of a limbal stem cell from the limbal explant onto the isolated Descemet's membrane, resulting in an isolated Descemet's membrane with limbal stem cells on its surface.

In some embodiments, separating the decellularized Descemet's membrane from the stroma of the cornea to obtain an isolated Descemet's membrane exposes the isolated Descemet's membrane to limbal stem cells found in the corneolimbal ring. For example, when the isolated Descemet's membrane is not excised (by trephination) or manually peeled from the corneolimbal ring, the isolated Descemet's membrane may be exposed to limbal stem cells found in the corneolimbal ring by removing the cornea stroma. In some embodiments, the corneolimbal ring remains attached to the isolated Descemet's membrane.

Additionally or alternatively, an isolated Descemet's membrane may be exposed to limbal stem cells obtained from another source or obtained from the same donor source but separated from the corneolimbal ring. In some embodiments, a limbal explant culture may be treated to release limbal stem cells (into a cell suspension) which may be seeded onto an isolated Descemet's membrane. In some embodiments, a limbal explant culture and/or a limbal tissue ring may be digested with one or more of trypsin (Sharifi, et al., *Biocell*. 2010; 34:53-55), dispase (Zhang, et al., Curr Eye Res. 2016; 41:318-325), or collagenase (Chen, et al., *Tissue Eng Part C Methods*. 2011; 17:537-548) to release the basal limbal stem cells (see FIG. 11A). In some embodiments, once in suspension, the limbal stem cells may be seeded onto an isolated Descemet's membrane without any further manipulation (see FIG. 11B). In some embodiments, the limbal stem cells may be sorted (for example, using flow cytometry) to select cells with a specific limbal stem cell marker or markers prior to being seeded onto an isolated Descemet's membrane. Exemplary methods of preparing limbal stem cells for culture on Descemet's membrane are described in Example 8A and 8B.

Limbal explant cultures and/or limbal stem cells may be maintained in any suitable growth media. Suitable growth media may include, for example, a growth medium containing human autologous serum, fetal bovine serum, human platelet lysates, and a growth medium containing serum-free medium with bovine pituitary extracts, growth supplement with recombinant components, or chemically defined supplements.

Figure 2E:
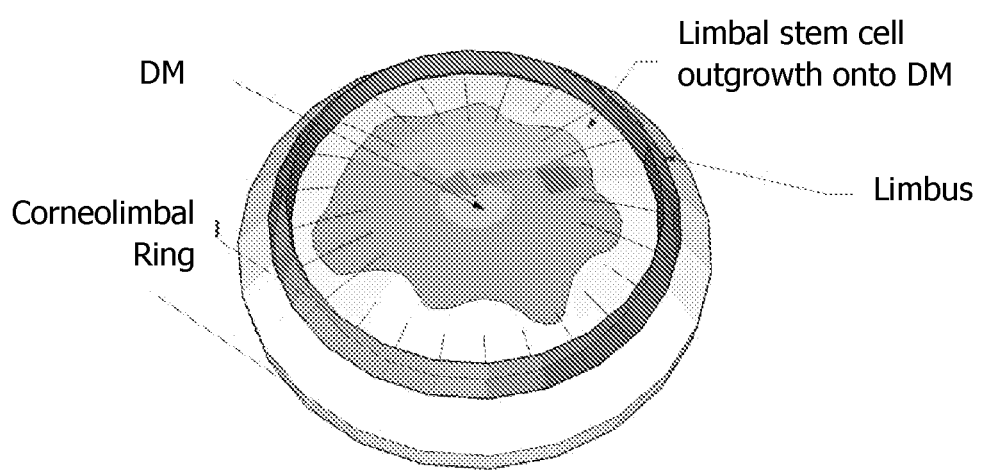

An isolated Descemet's membrane may be cultured under conditions that allow for growth of limbal stem cells (e.g., from a limbal explant and/or from a corneolimbal ring) onto the isolated Descemet's membrane. A drawing of one exemplary method of culturing Descemet's membrane to achieve limbal cell outgrowth onto the Descemet's membrane is shown in FIG. 2E. In some embodiments, the method may include making a partial-thickness incision in the corneolimbal ring to promote the outgrowth of limbal stem cells.

In some embodiments, the method may include placing the isolated Descemet's membrane in a cell culture media. The cell culture media may include any suitable cell culture media including, for example, an epithelial cell growth media or other media suitable for corneal organ culture. An exemplary media suitable for corneal organ culture is CorneaMax® (Eurobio, Les Ulis, France). In some embodiments, the cell culture media may be serum free. In some embodiments, including, for example, when the cell culture media is serum free, cell culture media may include pituitary extract. In some embodiments, the cell culture media may include one or more of a complex culture media supplemented with fetal bovine serum, a complex culture media supplemented with human serum, a complex culture media supplemented with platelet lysate serum, or a chemically-defined keratinocyte growth media. In some embodiments, the cell culture media may preferably promote limbal stem cell growth and/or maintain limbal stem cell pluripotency.

In some embodiments, the method may include incubating the isolated Descemet's membrane in the cell culture media under typical cell culture conditions including, for example, at a temperature in a range of 32° C. to 38° C. and/or at 5% $CO_2$. In some embodiments, the isolated Descemet's membrane is incubated with a limbal explant and/or a limbal stem cell.

Transplanting an Isolated Descemet's Membrane

In an additional aspect, this disclosure describes methods of transplanting an isolated Descemet's membrane to an ocular surface of a patient in need thereof.

Figure 2F:
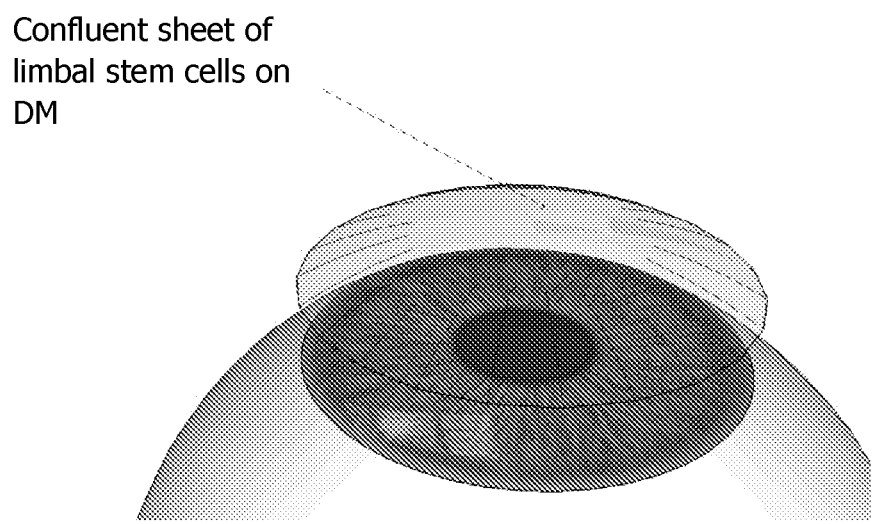
Figure 2G:
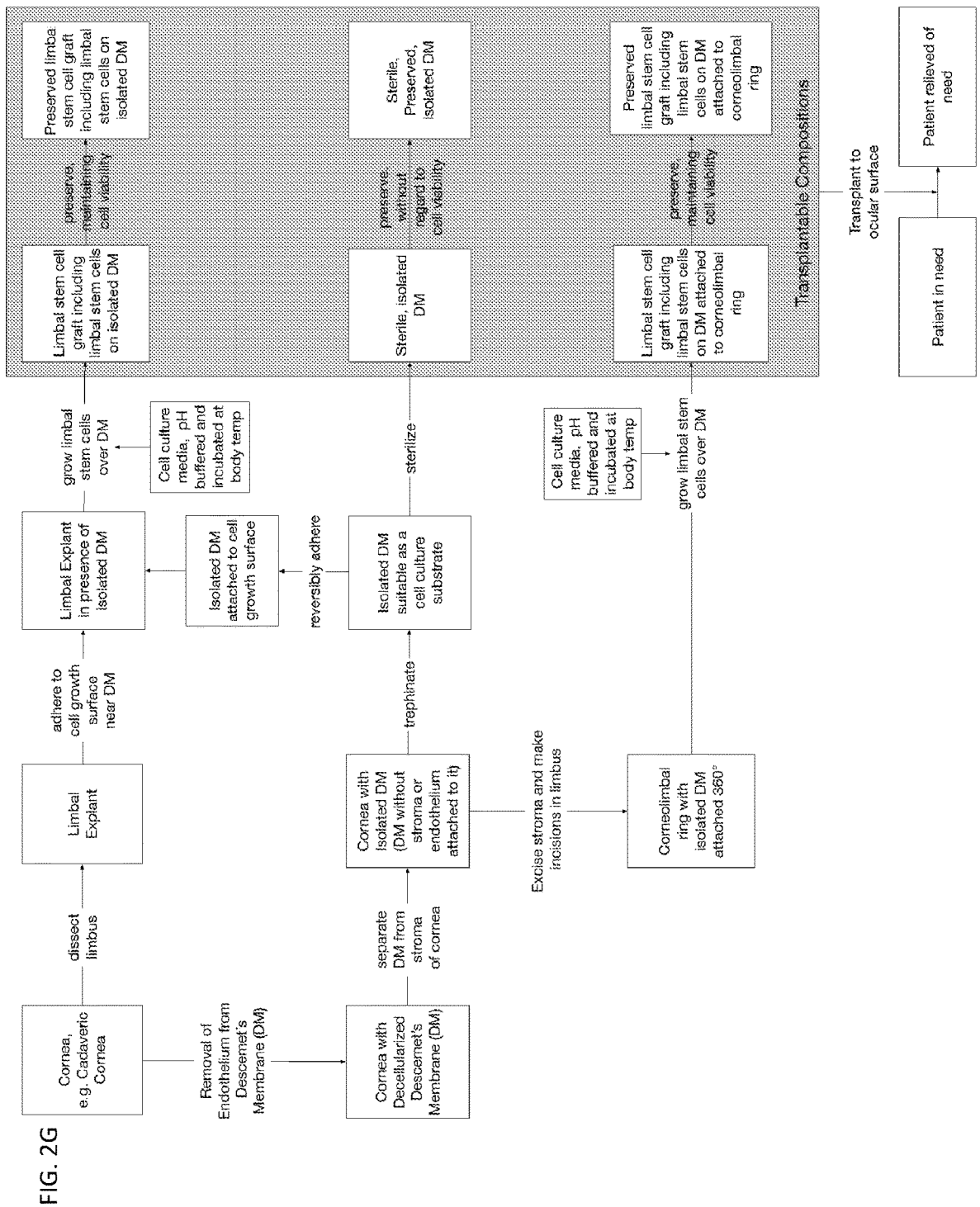

In some embodiments, the transplanted Descemet's membrane may be decellularized. In some embodiments, the transplanted Descemet's membrane may include limbal stem cells. A drawing of one exemplary method of transplanting a Descemet's membrane including limbal stem cells is shown in FIG. 2F. In some embodiments, the transplanted Descemet's membrane may include an isolated Descemet's membrane prepared by any of the methods described herein. For example, an isolated Descemet's membrane including limbal stem cells produced using the methods described herein may be transplanted to a patient exhibiting a partial limbal stem cell deficiency, a total limbal stem cell deficiency, a persistent epithelial defect, an epithelial erosion, a corneal ulcer, a corneal melt, and/or an ocular surface disease. Limbal stem cell deficiency may be caused by, for example, burns (chemical, thermal, or industrial); excessive use of certain medications; iatrogenic trauma, including, for example, overuse of contact lenses, chronic use of glaucoma drops, or ocular surgery; an autoimmune disease including, for example, Steven Johnson Syndrome or ocular cicatricial pemphigoid; or graft-versus-host disease (GVHD); etc.

In some embodiments, transplanting an isolated Descemet's membrane to an ocular surface of a patient, as described herein may have certain advantages over existing treatments for limbal stem cell deficiency. For example, transplanting an isolated Descemet's membrane to an ocular surface of a patient, as described herein (e.g., including a limbal stem cell), has certain advantages over an amniotic membrane-based CLET graft. A CLET-like procedure performed using an isolated Descemet's membrane is less expensive than an amniotic-membrane based method (because it takes advantage of the free Descemet's membrane that comes with every donor cornea and limbus), and it also makes it possible to produce CLET-like grafts in an eye bank setting, improving surgeon access to CLET technology.

Figure 7A:
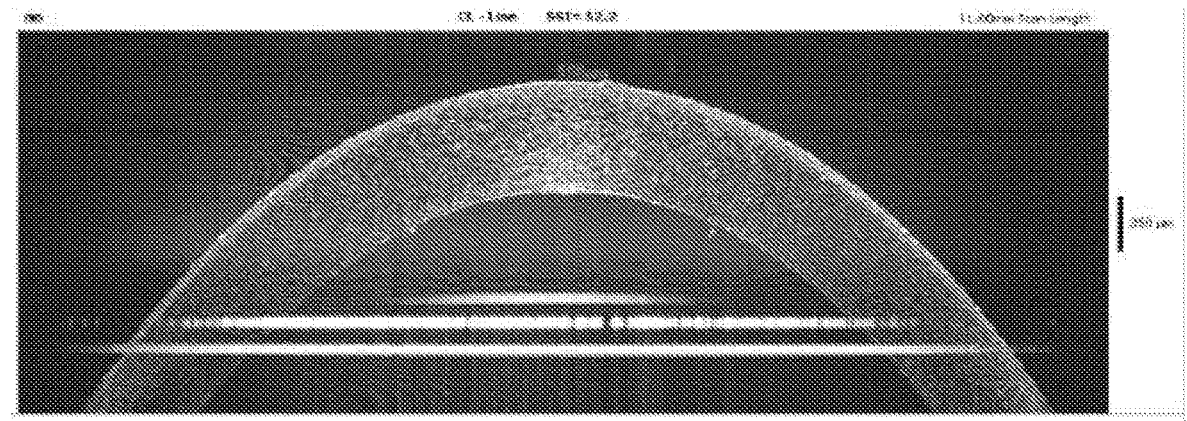
FIG. 7A-FIG. 7C show a series of optical coherence tomography (OCT) images that demonstrate that Descemet's membrane is resistant to collagenase digestion.

One of the major challenges of limbal stem cell transplantation is sustaining the long-term viability, proliferative potential, and overall stem cell phenotype of the transplanted cells outside of the native limbal niche microenvironment. As shown in FIG. 4 and Example 2, when used as a substrate, Descemet's membrane promotes rapid expansion of limbal stem cells in culture while maintaining the stem cell phenotype in the majority of cells out to several weeks in culture (based on cellular morphology and the expression of stem cell markers ABCG2 and ΔNp63α. Transplantation of Descemet's membrane along with limbal stem cells on the ocular surface provides a novel, viable technique for establishing a stable niche-like microenvironment on the cornea, and thus may provide a robust and promising technique for long-term reconstruction of the ocular surface. Additionally, intact Descemet's membrane is optically clear (see FIG. 5), resistant to collagenase digestion (see FIG. 7), minimally immunogenic when transplanted intraocularly, and freely available with every donor cornea from which stems cells are harvested.

In some embodiments, including, for example, when the isolated Descemet's membrane is decellularized, the isolated Descemet's membrane may be used as an ocular bandage including, for example, in patients with an ocular surface trauma, a recurrent erosion, a corneal melt, or a sterile corneal ulcer. Such patients may include any patient with a disease that compromises the ocular surface including, for example, patients with diabetes, patients with glaucoma, patients with injuries resulting from chronic contact lens wear, patients with complications of LASIK surgery, patients with neurotrophic concerns, patients with severe tear deficiency, and/or patients with exposure keratopathy.

For example, an isolated Descemet's membrane (with or without the presence of a limbal stem cell) may be useful as a reconstructive therapy in cases of minor ocular surface burns or trauma. For example, when the epithelium is damaged but enough of the native limbal stem cell population remains to regenerate the corneal epithelium, isolated Descemet's membrane (without a limbal stem cell), when placed as a resurfacing treatment, may establish a stable bandage layer on the ocular surface of the cornea that promotes regrowth of the patients' own epithelium in situ, while protecting the corneal stroma from enzymatic degradation by inflammatory mediators in the tear film due to its natural resistance to collagenase. Isolated Descemet's membrane can remain stable over long periods of time but is still transparent and visually unobstructive. Since the isolated Descemet's membrane is decellularized to remove endothelial cells, the isolated Descemet's membrane has no cells for the body to reject making the risk of rejection minimal.

Isolated Descemet's membrane may be adhered to the recipient cornea by any suitable means. In some embodiments, the Descemet's membrane may be adhered to the recipient cornea by air drying. In some embodiments, the Descemet's membrane may be adhered to the recipient cornea using one or more of a fibrin sealant, colloidal silica nanoparticles, and light-initiated rose bengal collagen cross-linking.

Compositions Including an Isolated Descemet's Membrane

In another aspect, this disclosure describes a composition that includes an isolated Descemet's membrane, wherein the Descemet's membrane has been decellularized and separated from the corneal stroma.

In some embodiments, the composition further includes a limbal stem cell. In some embodiments, the limbal stem cell and the isolated Descemet's membrane are from the same cornea. The limbal stem cell may, in some embodiments, be in contact with (for example, present on the surface of) the isolated Descemet's membrane.

In some embodiments, the composition includes isolated Descemet's membrane attached to a corneolimbal ring. In some embodiments, the composition includes a limbal stem cell, the limbal stem cell may be present in the corneolimbal ring and/or on the surface of the isolated Descemet's membrane that has been bared to the corneolimbal ring.

In some embodiments, the isolated Descemet's membrane may act as a substrate for the limbal stem cell.

In some embodiments, the isolated Descemet's membrane may have been sterilized or preserved or both.

Exemplary Method Embodiments

1. A method comprising:
    removing endothelium from a Descemet's membrane of a cornea to provide a decellularized Descemet's membrane; and
    separating the decellularized Descemet's membrane from the stroma of the cornea to obtain an isolated Descemet's membrane.
2. The method of Embodiment 1, wherein the cornea comprises a cadaveric cornea.
3. The method of any one of the preceding Embodiments, wherein the cornea is human or porcine.
4. The method of any one of the preceding Embodiments, wherein removing endothelium from a Descemet's membrane comprises at least one of mechanical, enzymatic, or chemical decellularization.
5. The method of any one of the preceding Embodiments, wherein separating the decellularized Descemet's membrane from the stroma of the cornea comprises injecting fluid or air or both into the cornea.
6. The method of any one of the preceding Embodiments, wherein separating the decellularized Descemet's membrane from the stroma of the cornea comprises manual peeling of Descemet's membrane from the stroma of the cornea.
7. The method of any one of the preceding Embodiments, the method further comprising using the isolated Descemet's membrane as a cell culture substrate.
8. The method of Embodiment 7, wherein the method comprises using the isolated Descemet's membrane as a cell culture substrate to support proliferation of a limbal stem cell.
9. The method of Embodiment 8, wherein the limbal stem cell adheres to the isolated Descemet's membrane.
10. The method of any one of the preceding Embodiments, the method comprising reversibly attaching the isolated Descemet's membrane to a cell culture surface.
11. The method of any one of the preceding Embodiments, the method comprising culturing a limbal explant in the presence of the isolated Descemet's membrane.
12. The method of Embodiment 11, wherein the limbal explant comprises a corneolimbal ring, and wherein the limbal explant is cultured under conditions that allow outgrowth of limbal stem cells from the corneolimbal ring onto the isolated Descemet's membrane.
13. The method of any one of Embodiments 1 to 10, wherein separating the decellularized Descemet's membrane from the stroma of the cornea to obtain an isolated Descemet's membrane comprises exposing the isolated Descemet's membrane to a limbal stem cell.
14. The method of Embodiment 13, wherein exposing the isolated Descemet's membrane to the limbal stem cell comprises exposing the isolated Descemet's membrane to the corneolimbal ring of the cornea.
15. The method of any one of Embodiments 11 to 14, wherein the method further comprises making a partial-thickness incision in the corneolimbal ring to promote outgrowth of limbal stem cells.
16. The method of any one of the preceding Embodiments, wherein the method comprises placing the isolated Descemet's membrane, a limbal explant, and/or a limbal stem cell in a cell culture media.
17. The method of Embodiment 16, wherein the cell culture media promotes limbal stem cell growth and/or maintains limbal stem cell pluripotency.
18. The method of Embodiment 16 or 17, wherein the method comprises incubating the isolated Descemet's membrane and a limbal stem cell in the cell culture media at a temperature in a range of 32° C. to 38° C.
19. The method of any one of the preceding Embodiments, wherein the method further comprises sterilizing the isolated Descemet's membrane.

20. The method of any one of the preceding Embodiments, wherein the method further comprises one or more of freezing, lyophilizing, and cryopreserving the isolated Descemet's membrane.

21. The method of any one of the preceding Embodiments, wherein the method further comprises transplanting the isolated Descemet's membrane of any one of the previous Embodiments to an ocular surface of a patient in need thereof.

22. The method of Embodiment 21, wherein the patient exhibits at least one of a partial limbal stem cell deficiency, a total limbal stem cell deficiency, a persistent epithelial defect, an epithelial erosion, a corneal ulcer, a corneal melt, or an ocular surface disease.

23. The method of Embodiment 21, wherein the patient exhibits at least one of an ocular surface trauma, a recurrent erosion, a corneal melt, or a sterile corneal ulcer.

Exemplary Composition Embodiments

1. A composition comprising:
    an isolated Descemet's membrane, wherein the Descemet's membrane has been decellularized and separated from the corneal stroma.
2. The composition of Embodiment 1, wherein the composition further comprises a limbal stem cell.
3. The composition of Embodiment 2, wherein the limbal stem cell is in contact with the isolated Descemet's membrane.
4. The composition of Embodiment 3, wherein the isolated Descemet's membrane acts as a substrate for the limbal stem cell.
5. The composition of any preceding Embodiment, wherein the isolated Descemet's membrane has been sterilized or preserved or both.
6. The composition of any one of Embodiments 2 to 5, wherein the composition comprises a corneolimbal ring, and further wherein the limbal stem cell is present in the corneolimbal ring.
7. The composition of any one of Embodiments 2 to 6, wherein the limbal stem cell and the isolated Descemet's membrane are from the same cornea.
8. The composition of any one of Embodiments 2 to 6, wherein the limbal stem cell and the isolated Descemet's membrane are from different corneas.

The present invention is illustrated by the following examples. It is to be understood that the particular examples, materials, amounts, and procedures are to be interpreted broadly in accordance with the scope and spirit of the invention as set forth herein.

EXAMPLES

Example 1

Figure 3A:
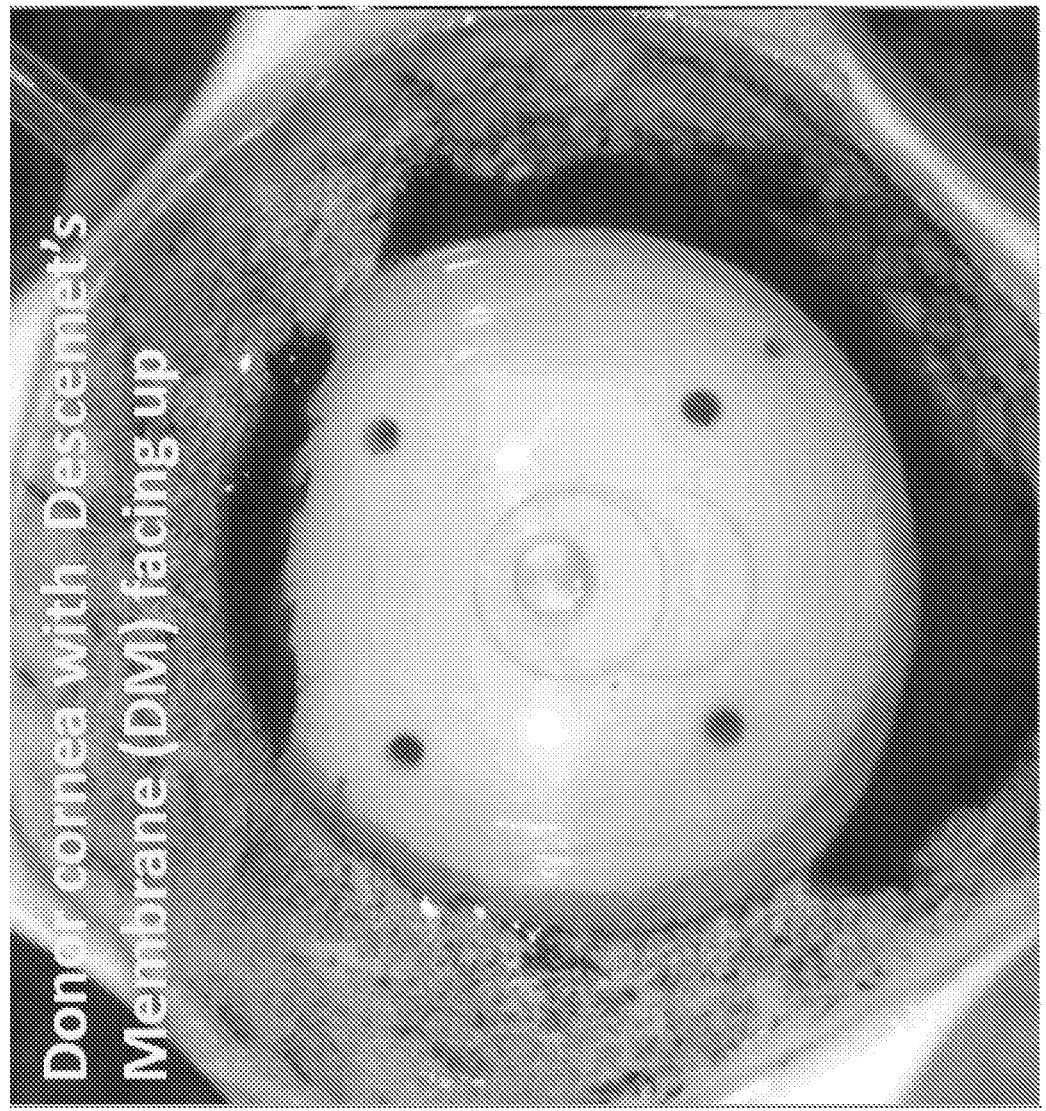
FIG. 3A-FIG. 3F show images of a cornea before, during, and after Descemet's membrane has been separated from the stroma of a cornea according to a method described herein.
Figure 3B:
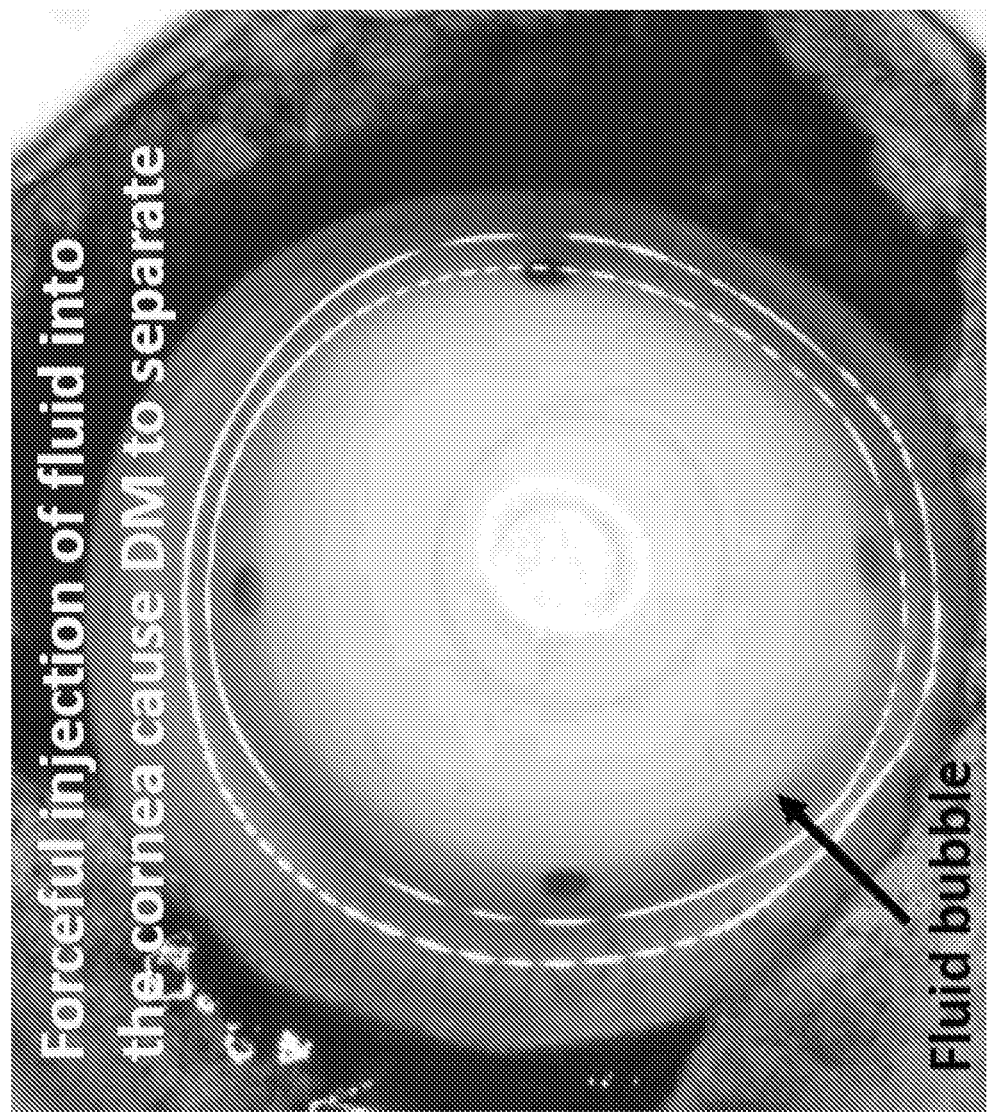
Figure 3C:
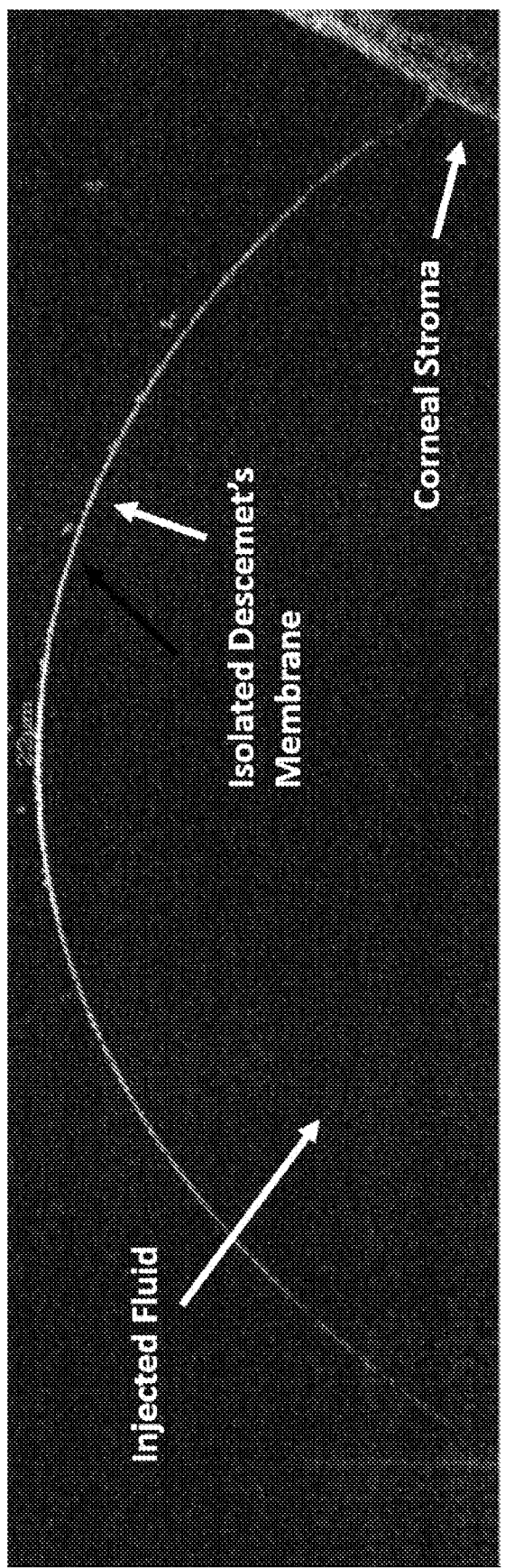

This Example describes a method for the isolation of a Descemet's membrane from the stroma of a cornea, to form an isolated Descemet's membrane, as shown in one embodiment in FIG. 2 & FIG. 3B-FIG. 3C.

First, the endothelium was removed from Descemet's membrane by mechanical debridement to form a decellularized Descemet's membrane. Then, the decellularized Descemet's membrane was isolated from the stroma of a cornea by manually injecting cornea storage solution with pressure not exceeding 600 mmHg into the posterior stroma, near Descemet's membrane. A super sharp blade was used to make an incision through the stroma. Scissors were used to perform a continuous circumferential cut to excise the residual cornea while leaving the corneolimbal ring attached to isolated Descemet's membrane.

In some instances, the Descemet's membrane was then excised from the corneolimbal ring using a trephine. In some instances, the Descemet's membrane was decontaminated by exposure to a 5% povidone iodide solution.

Example 2

This Example describes a method for the separation of a Descemet's membrane from the stroma of a cornea, and an exemplary method for using the isolated Descemet's membrane as a cell culture substrate for culturing a limbal stem cell, as shown in one embodiment in FIG. 2.

Figure 3D:
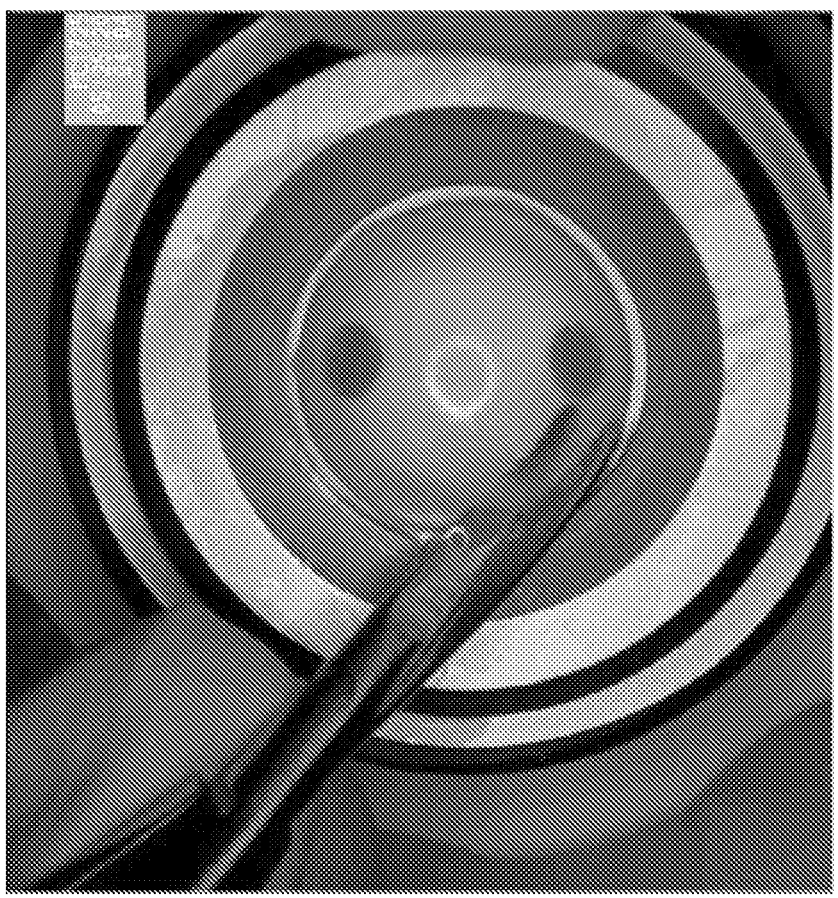

Isolated Descemet's membrane was prepared as described in Example 1. The residual cornea was excised, exposing the isolated Descemet's membrane to the corneolimbal ring, as shown in one embodiment in FIG. 3D.

Figure 3E:
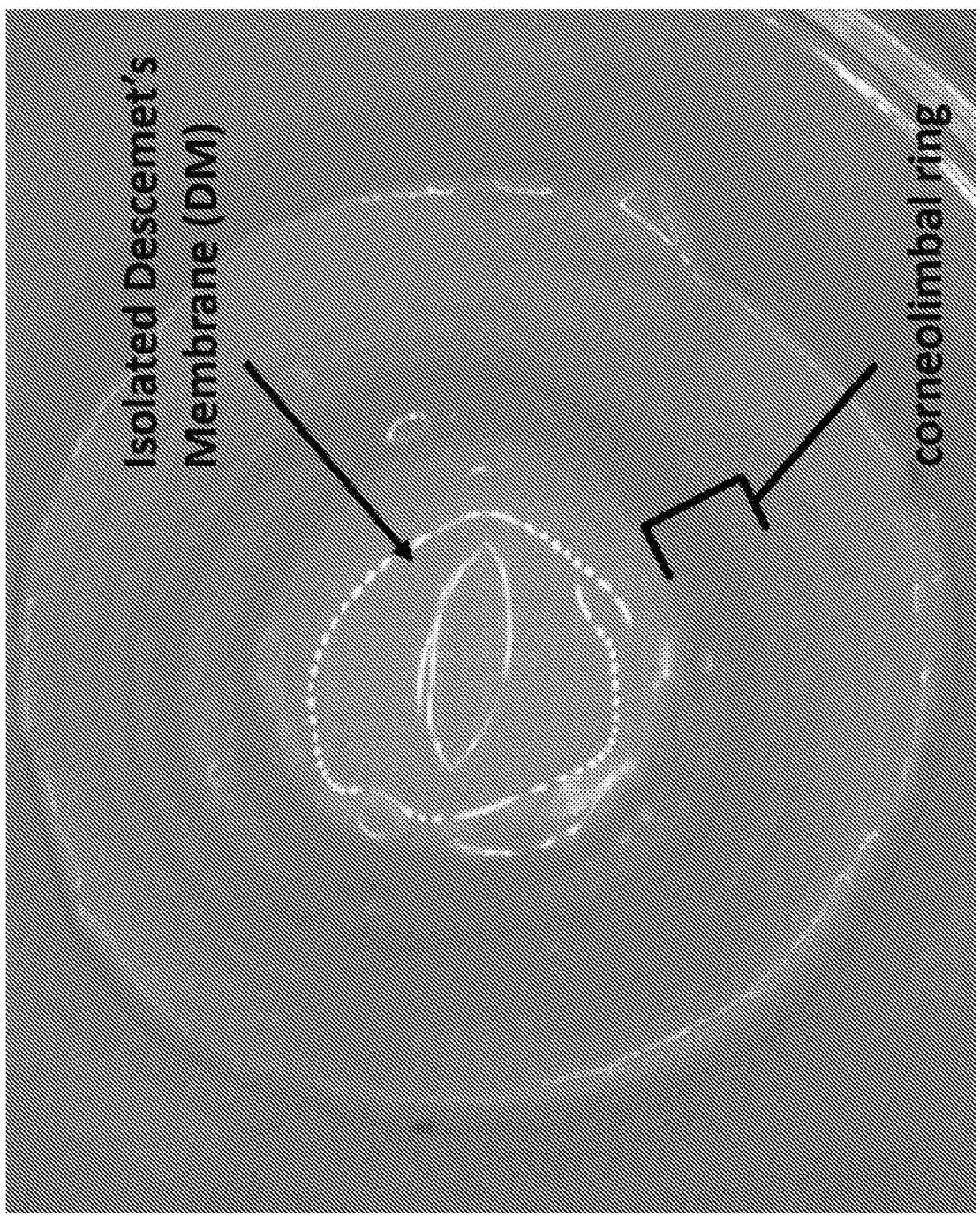
Figure 3F:
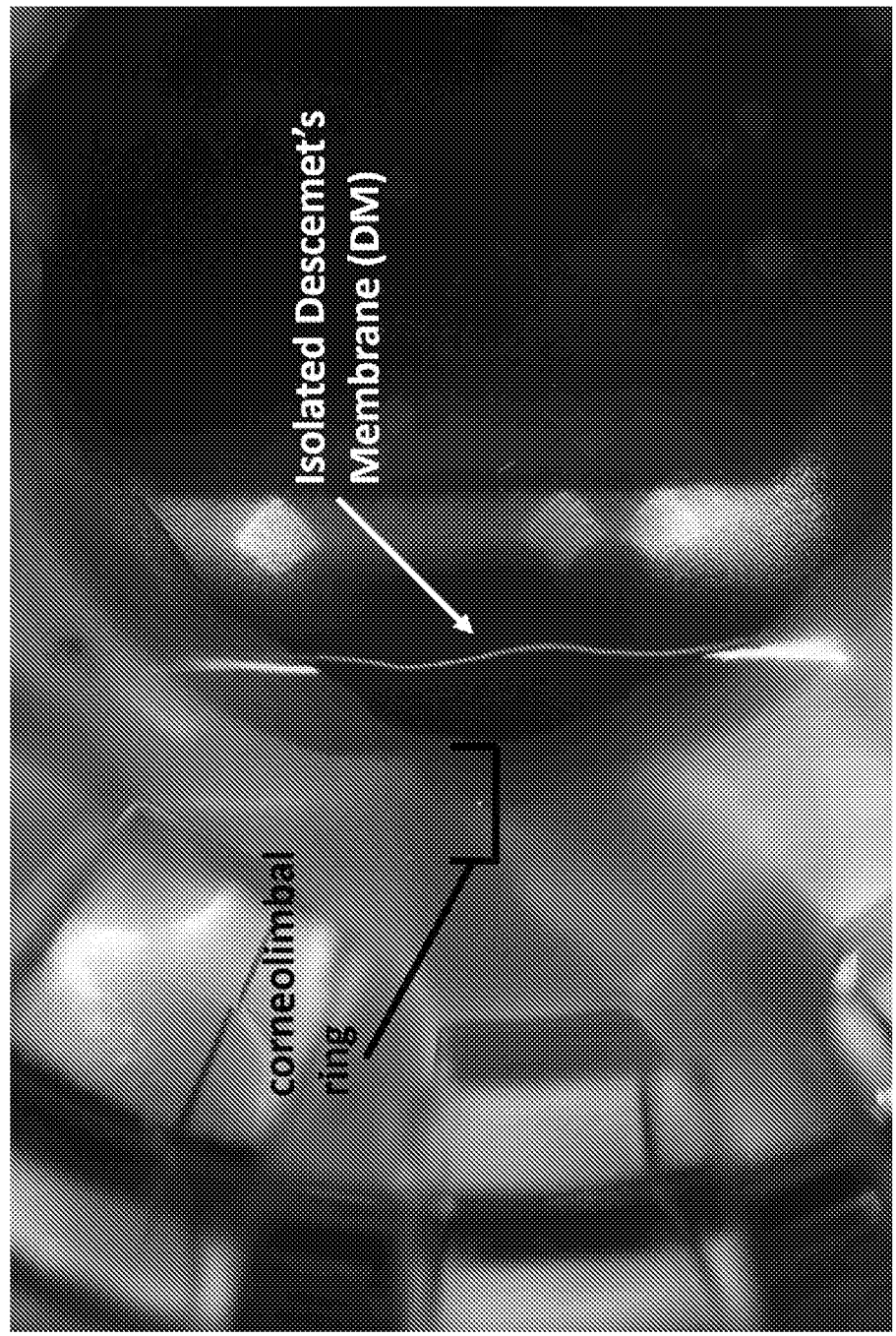

The isolated Descemet's membrane (FIG. 3E) was placed in complex culture media supplemented with fetal bovine serum and cultured at 37° C., 5% $CO_2$ for up to 4 weeks. Cells grew out from the corneolimbal ring and grew over the isolated Descemet's membrane (FIG. 3F).

Figure 4A:
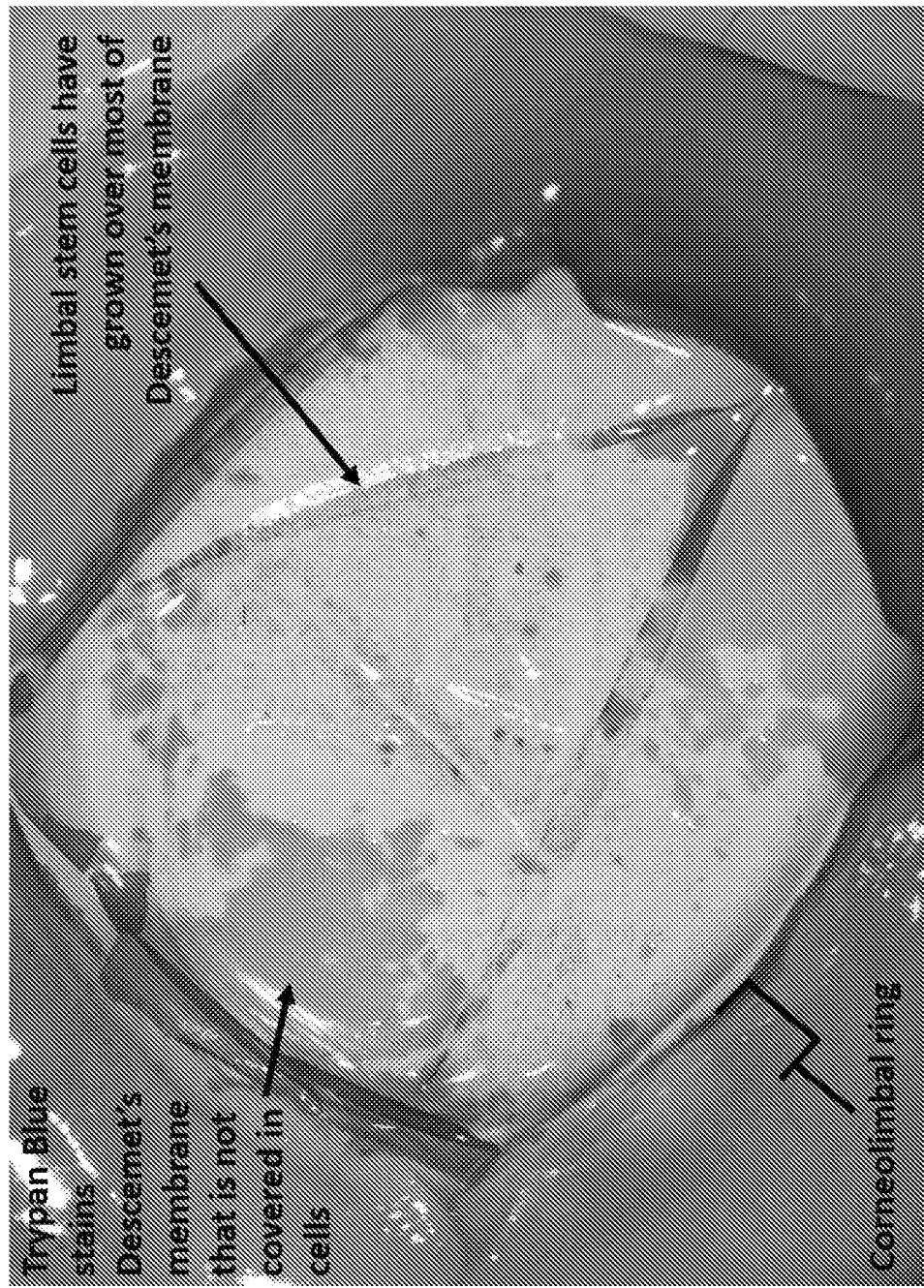
FIG. 4A-FIG. 4F show images that demonstrate growth of limbal stem cells from the intact corneolimbal ring onto isolated Descemet's membrane after Descemet's membrane has been exposed according to a method described herein.
Figure 4B:
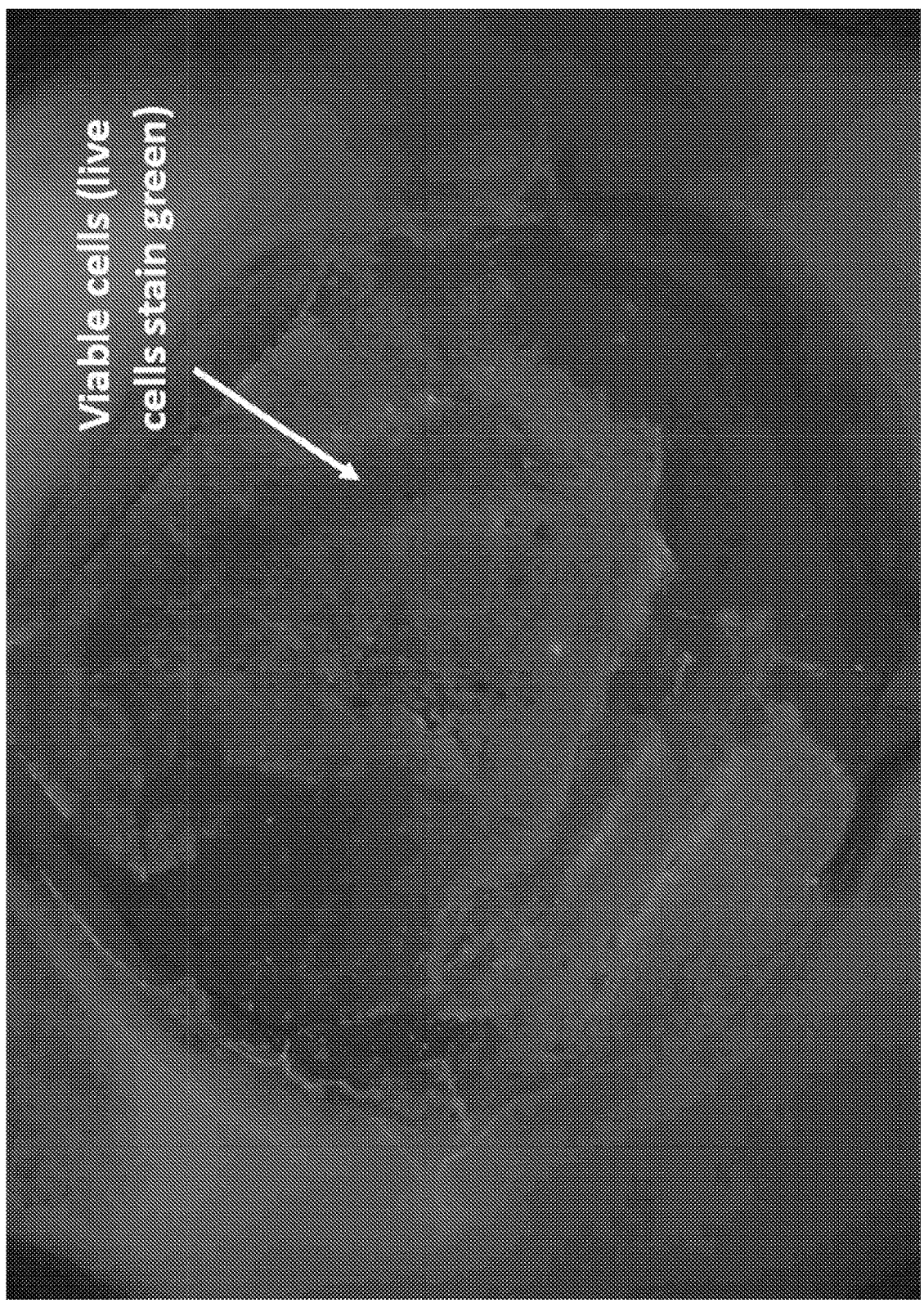
Figure 4C:
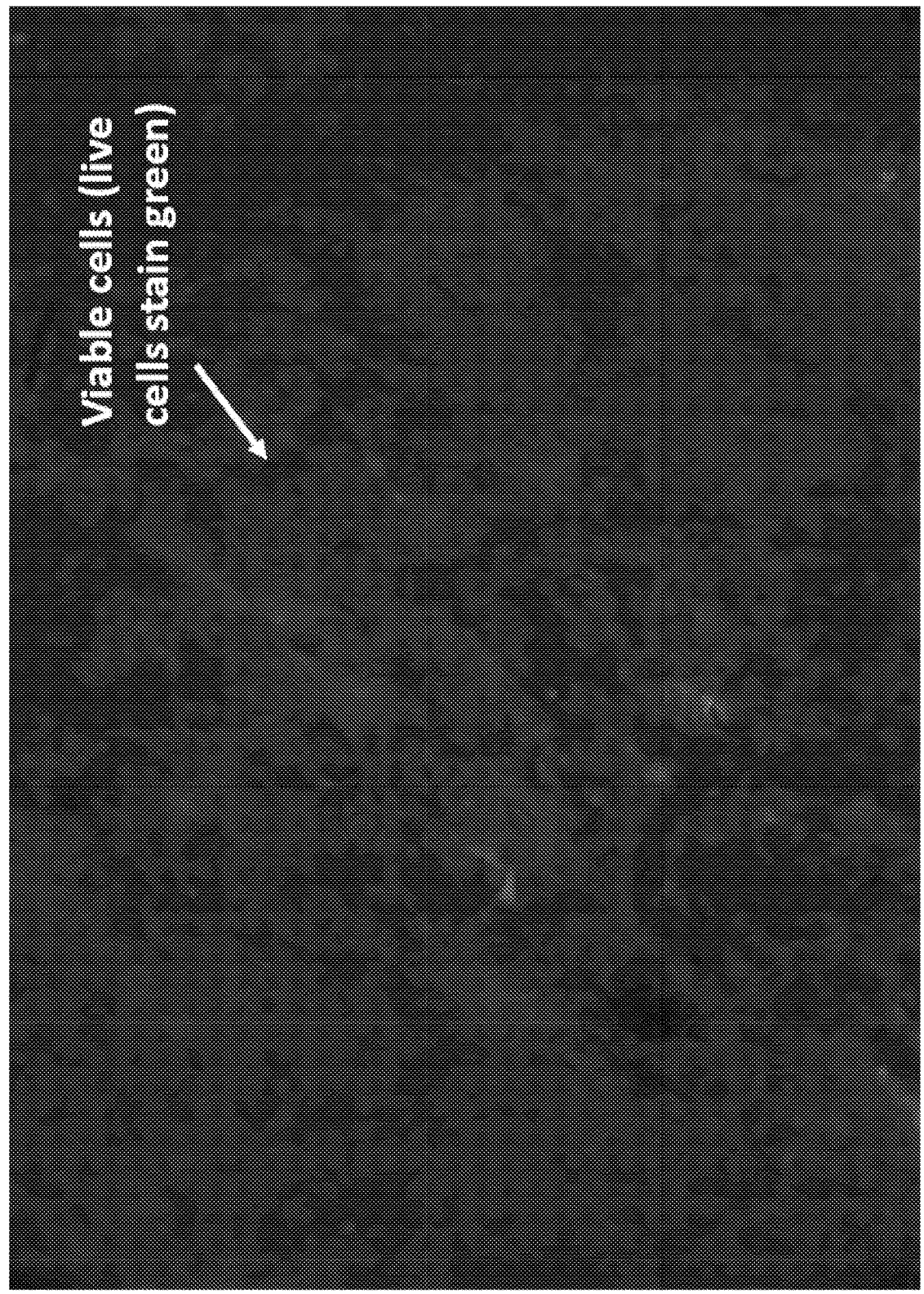

The resulting cultures were stained with 0.06% Trypan Blue for 1 minute or 2 µM Calcein AM for 20 minutes. As shown in FIG. 4A-FIG. 4C, viable cells (which exclude Trypan blue or are stained green) grew over most of the isolated Descemet's membrane in 1 week.

Figure 4D:
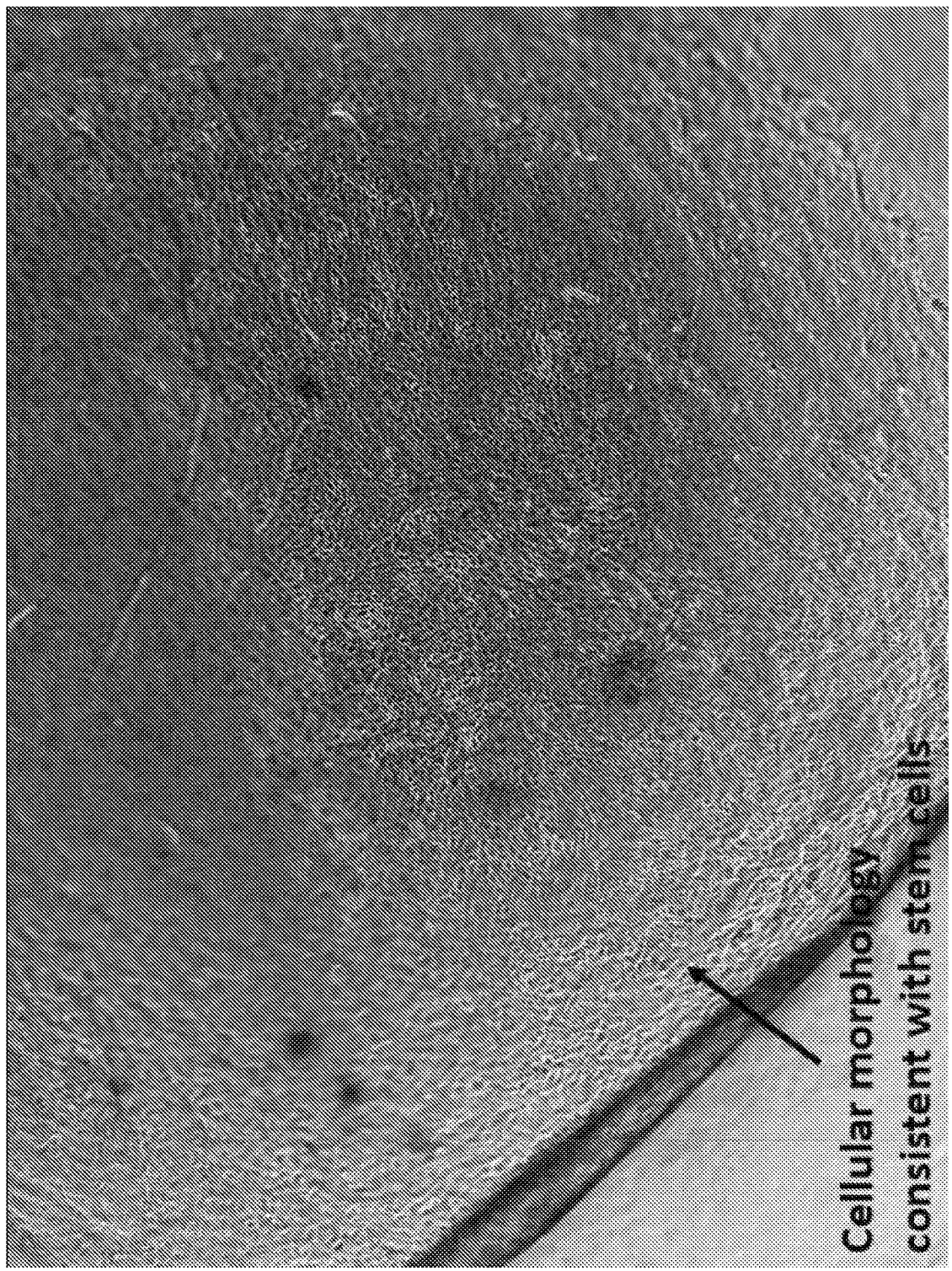
Figure 4E:
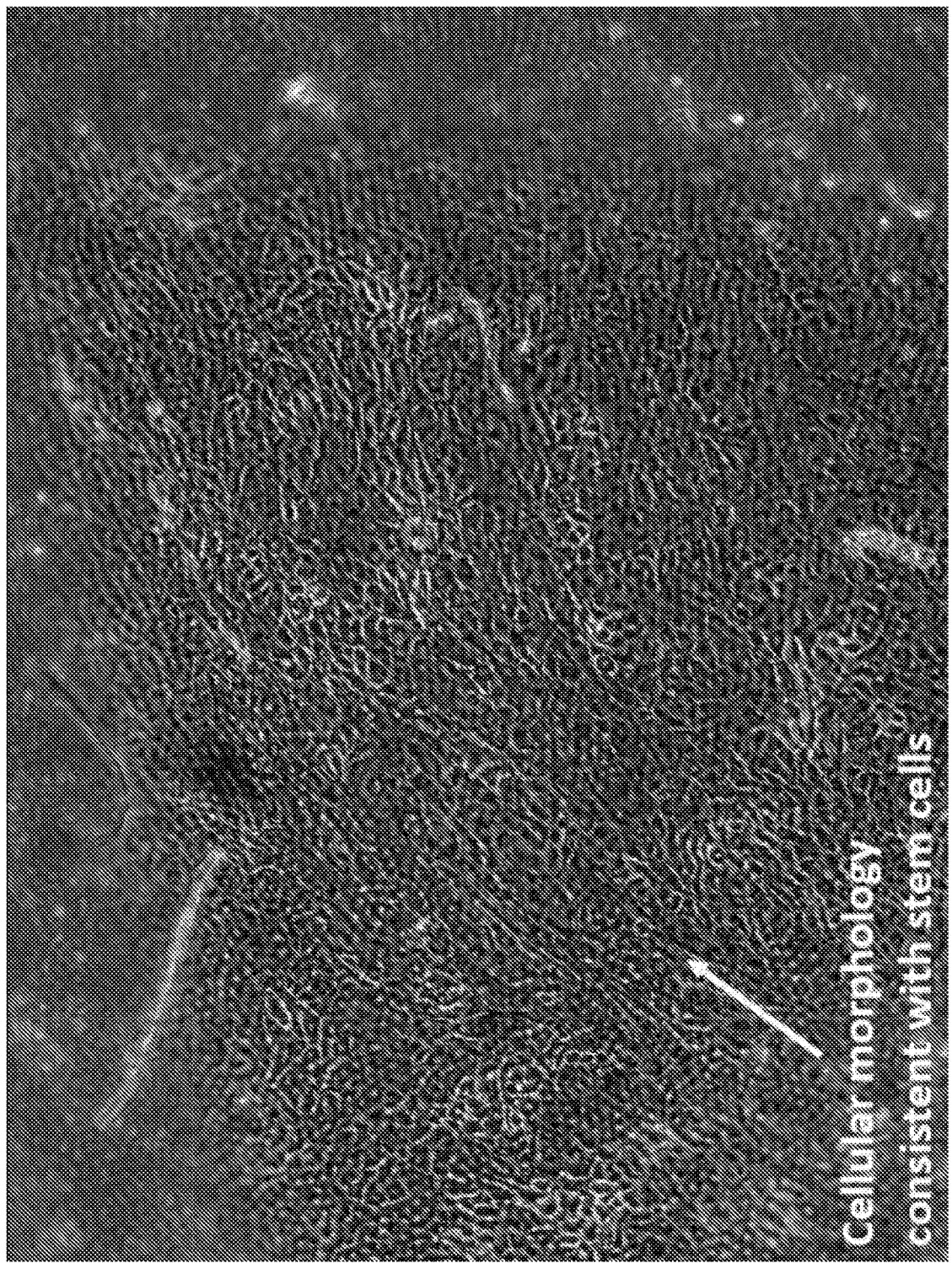

As shown in FIG. 4D-FIG. 4E, the cellular morphology of the cells growing on the isolated Descemet's membrane at 1 week was consistent with limbal stem cells rather than fibroblasts.

Figure 4F:
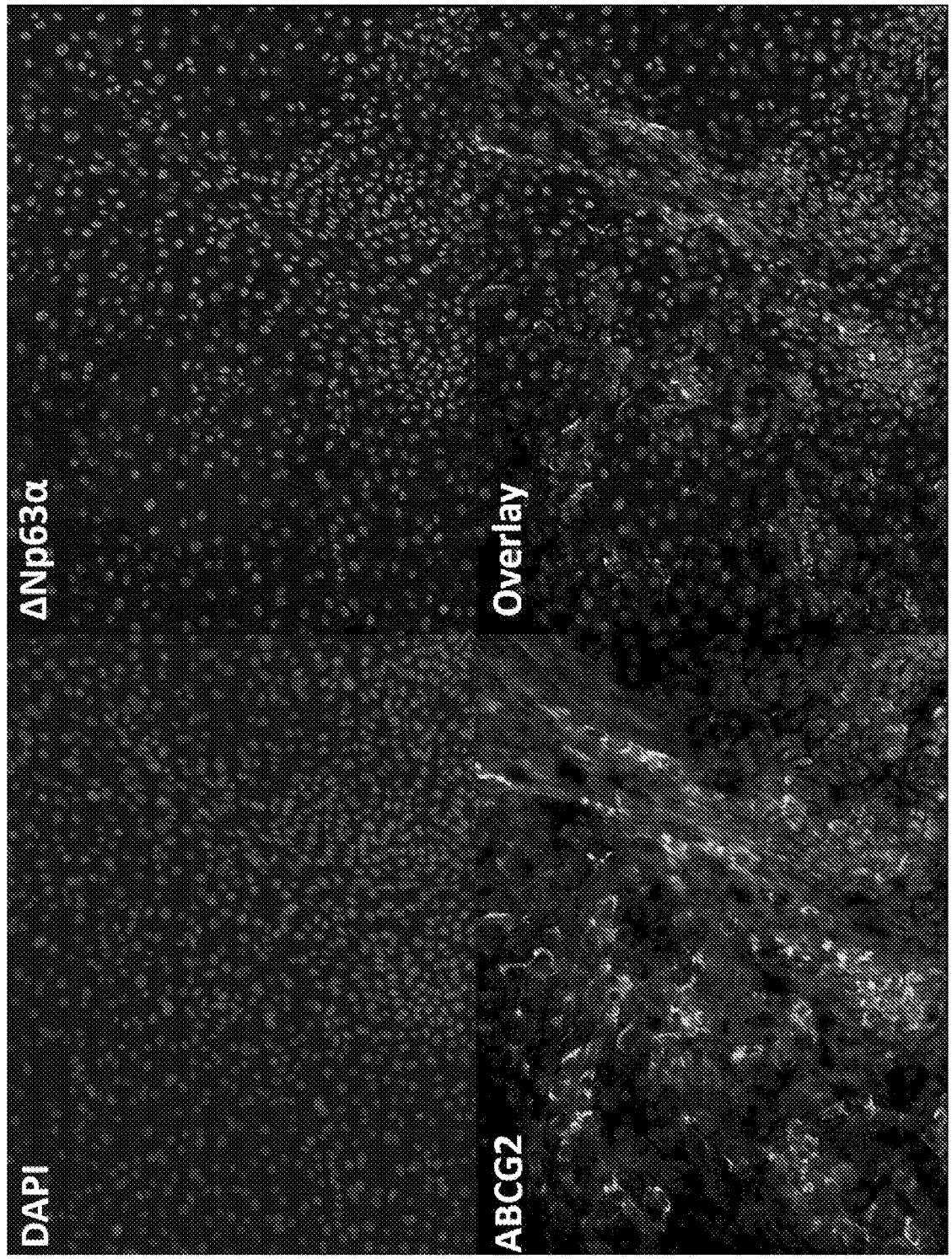

The resulting cultures were stained using the methods described by Suri et al. *Curr Eye Res.* 2016; 41:1266-1273. As shown in FIG. 4F, the cells growing on the isolated Descemet's membrane express $\Delta Np63\alpha$ and ABCG2, stem cell biomarkers, after 1 week in culture.

Example 3

Figure 5A:
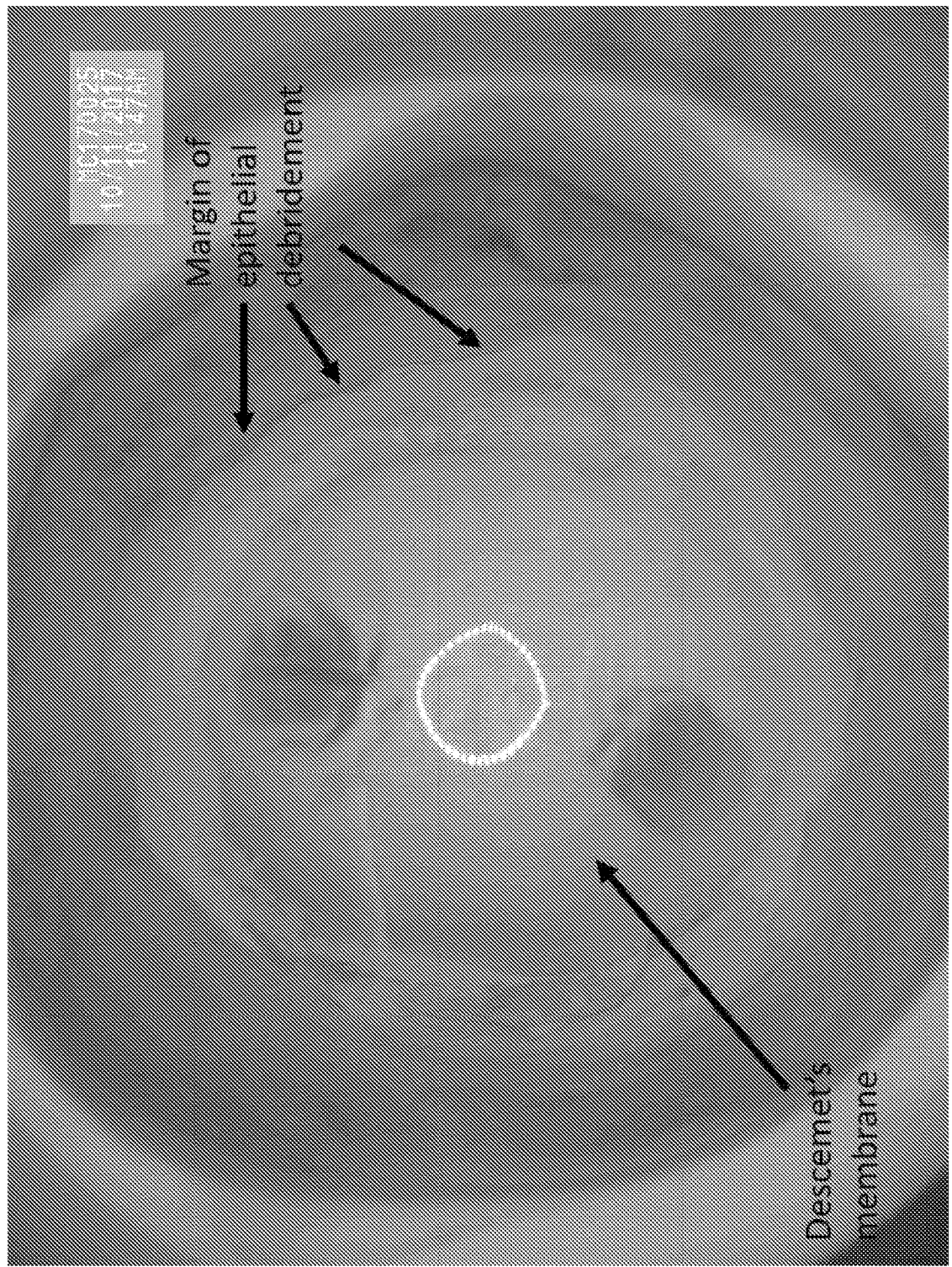
FIG. 5A shows a top view of a Descemet's membrane transplanted onto a donor cornea and stained with Trypan blue (to assist in visualization); the Descemet's membrane is clear and conforms well to the anterior surface of the cornea.
Figure 5B:
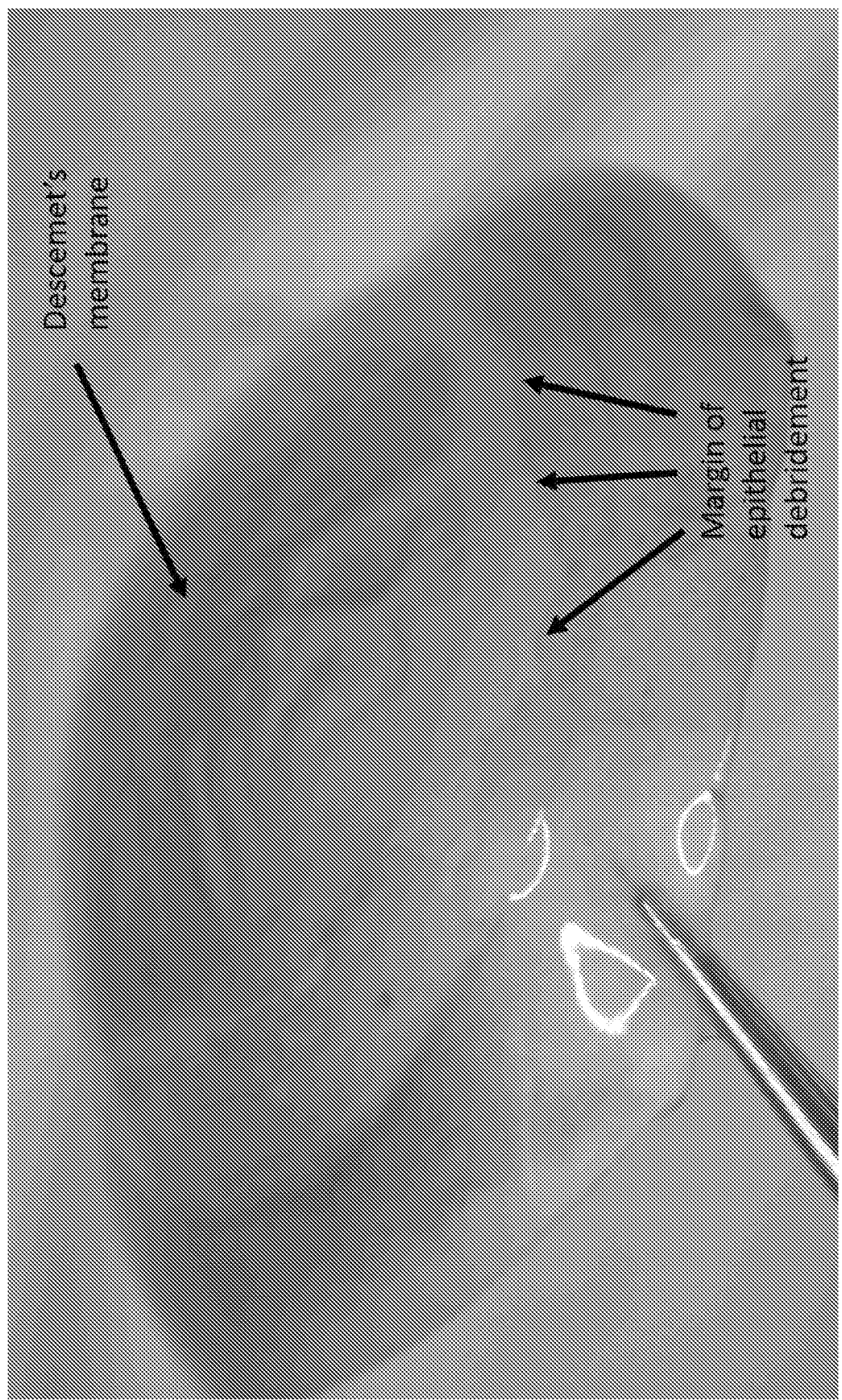
FIG. 5B shows an oblique view of Descemet's membrane transplanted onto a donor cornea and stained with Trypan blue; the Descemet's membrane is clear and conforms well to the anterior surface of the cornea.
Figure 6:
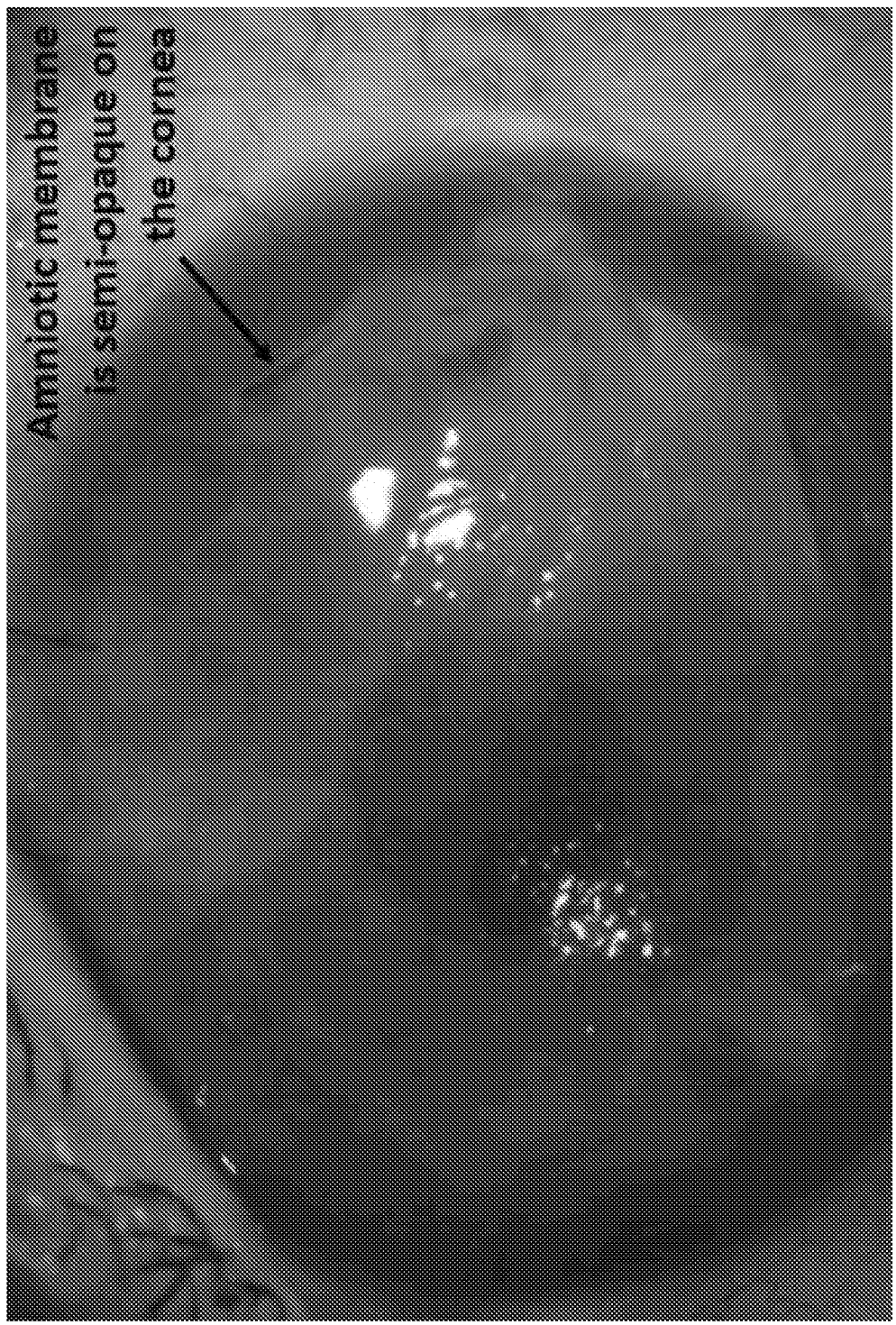
FIG. 6 shows an image of a human amniotic membrane transplanted onto a patient's cornea, demonstrating the semi-opacity of the amniotic membrane as reported by Connon et al., Br J Ophthalmol. 2010; 94:1057-1061.

Isolated Descemet's membrane excised from the corneolimbal, prepared as described in Example 1, was transplanted onto a recipient cornea after mechanical debridement of the epithelial layer of the recipient cornea. The isolated Descemet's membrane was stained with 0.06% Trypan blue for 1 minute before transplantation to assist in visualization. Descemet's membrane was adhered to the recipient cornea by air drying. As shown in FIG. 5, the Descemet's membrane is transparent. In contrast, as shown in FIG. 6, an amniotic membrane, transplanted onto a cornea, is semi-opaque as described by Connon, et al., *Br J Ophthalmol.* 2010; 94:1057-1061.)

Example 4

This Example shows Descemet's membrane is resistant to enzymatic degradation.

Figure 7B:
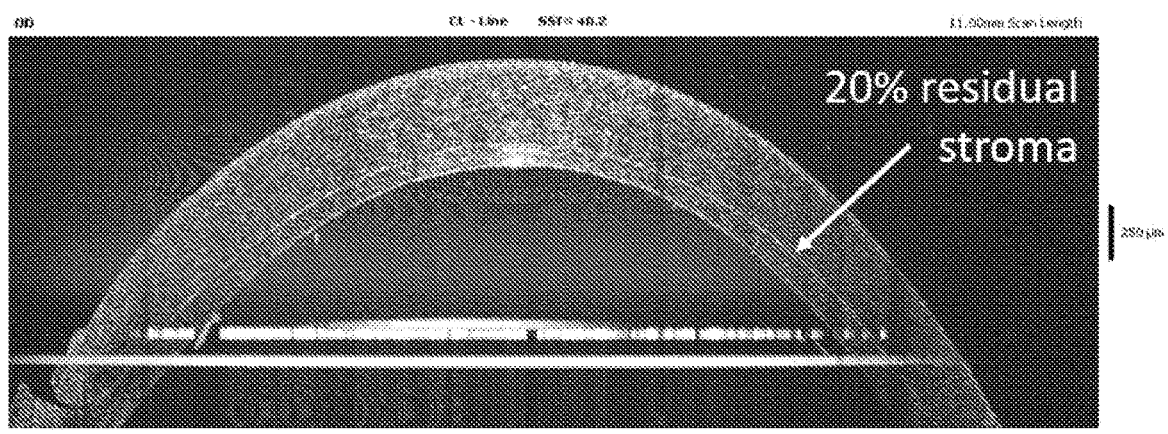
Figure 7C:
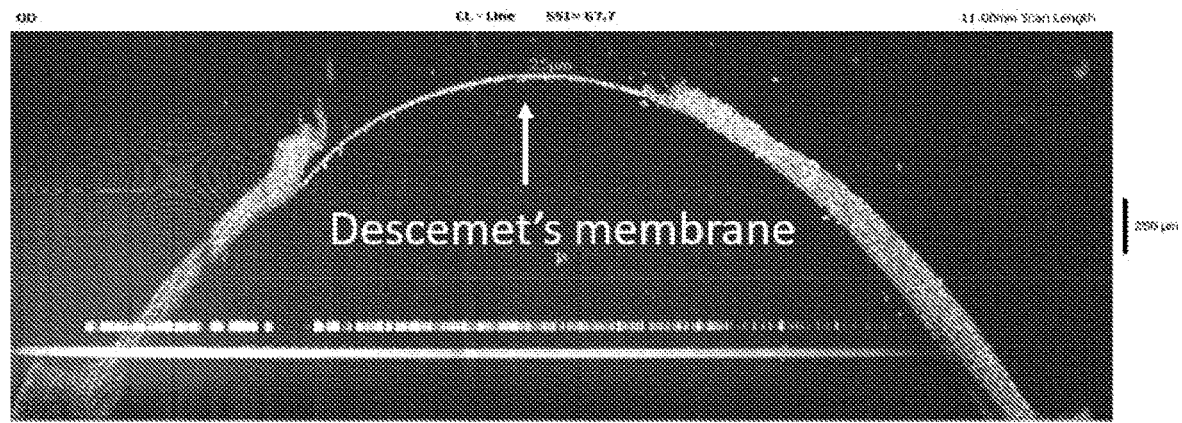

A donor cornea (see FIG. 7A) was cut down with a microkeratome to 20% thickness to reduce the total time for collagenase to digest the corneal stroma (FIG. 7B). The residual stroma bed was then treated for 45 minutes with collagenase A. After collagenase treatment, the stroma was completely digested, but the Descemet's membrane remained intact (FIG. 7C).

Example 5

Isolated Descemet's membrane, prepared as described in Example 1, was allowed to dry onto a treated polystyrene tissue culture surface. Corneolimbal ring was minced into 1 mm² limbal explant fragments and adhered on the tissue culture plastic surface near Descemet's membrane. Complex culture media supplemented with fetal bovine serum was added. The limbal explants and Descemet's membrane were then cultured at 37° C. and 5% $CO_2$. Culture media was changed every 48 hours. Limbal stem cells proliferated out from the limbal explant fragments over the tissue culture plastic and onto the Descemet's membrane.

After 5 days, cells were immunostained, as described in FIG. 4 and Example 2, for their expression of ΔNp63α and ABCG2 to confirm limbal stem cell phenotype. In a confluent culture of cells growing over both tissue culture plastic and Descemet's membrane, cells on Descemet's membrane showed greater expression of putative limbal stem cell markers, ΔNp63α and ABCG2.

Figure 8:
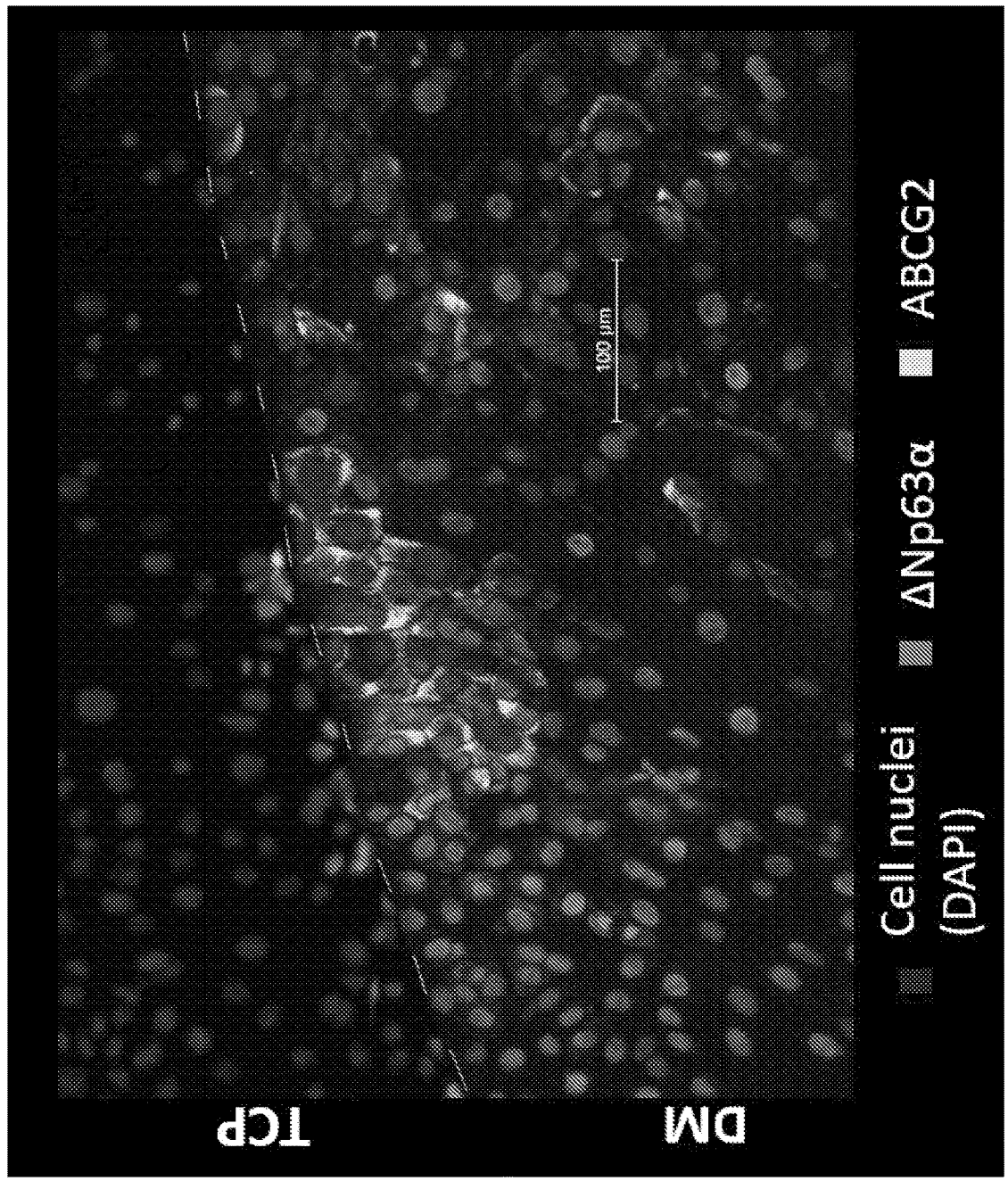
FIG. 8 shows an image that demonstrates Descemet's membrane's ability to support limbal stem cells in culture. Immunofluorescence staining shows expression of limbal stem cell markers, $\Delta Np63\alpha$ (red/pink) and ABCG2 (green), in cells cultured from limbal explants on Descemet's membrane (DM, below the dashed line), but not on tissue culture plastic (TCP, above the dashed line). The DAPI (blue) immunofluorescence stain indicates all cell nuclei.

Results are shown in FIG. 8.

Example 6

Isolated Descemet's membrane excised from the corneolimbal ring, prepared as described in Example 1, was transplanted onto a cornea after mechanical debridement of the recipient cornea epithelium as described in Example 3. The cornea was then placed in complex culture media supplemented with fetal bovine serum and incubated at 37° C. and 5% $CO_2$. Corneal epithelium regrew over the Descemet's membrane after one week. The cornea was then assessed by immunohistochemistry to evaluate the presence of Descemet's membrane (PAS positive immunostaining) and corneal epithelium (pancytokeratin positive immunostaining) on the surface of the cornea.

Figure 9:
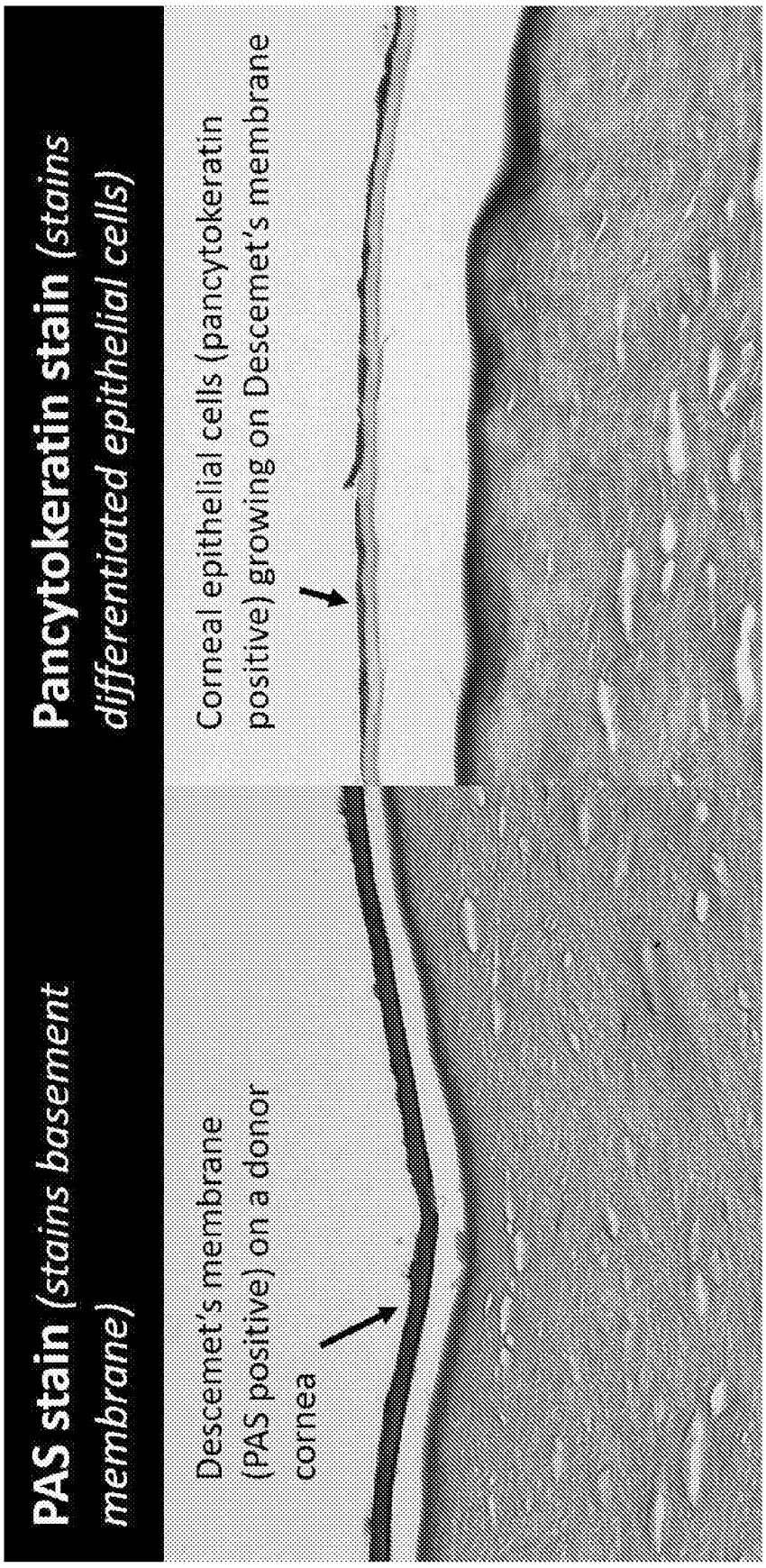
FIG. 9 shows the ability of Descemet's membrane to support growth of corneal epithelial cells on the surface of a cornea in an organ culture model. The left panel shows immunostaining with periodic acid-Schiff (PAS), indicating the presence of Descemet's membrane on the surface of the cornea. The right panel shows immunostaining with pancytokeratin, indicating corneal epithelial cells growing over Descemet's membrane.

Results are shown in FIG. 9. These result support the ability of Descemet's membranes to act as an ocular surface bandage to promote corneal epithelial healing.

Example 7

Figure 10:
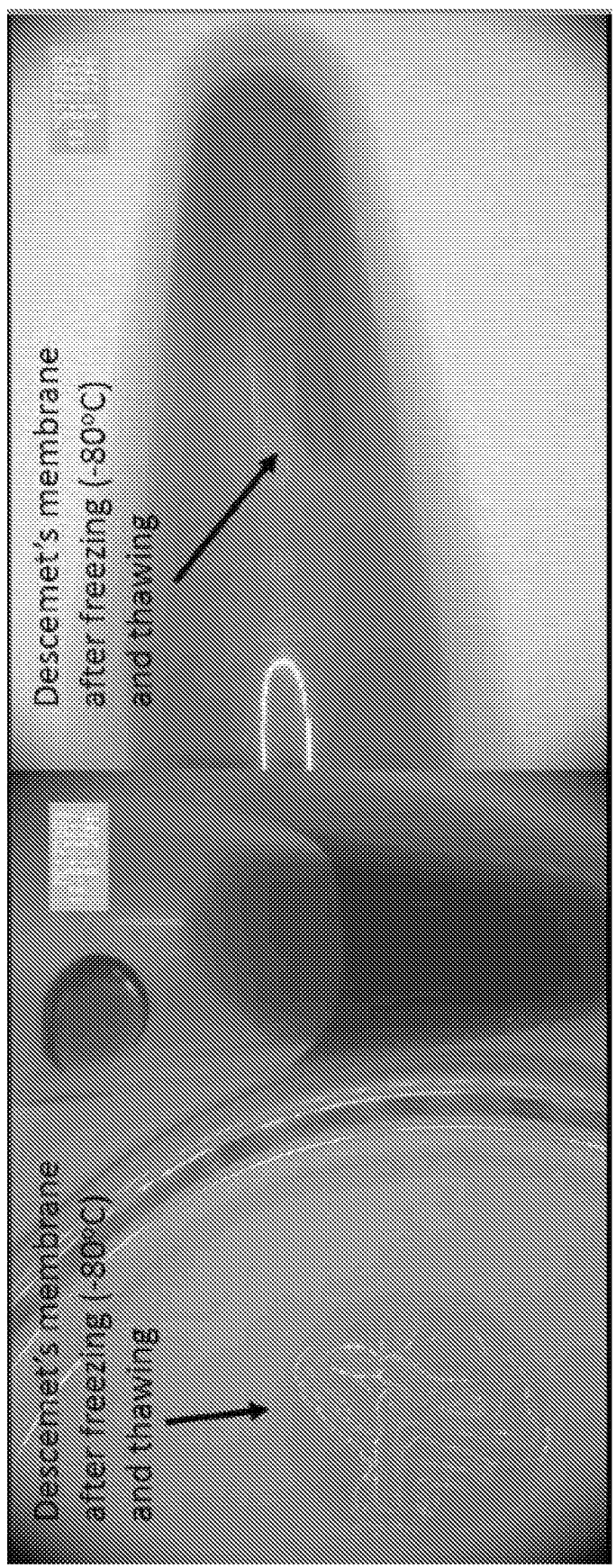
FIG. 10 shows exemplary Descemet's membranes from donor corneas stained with Trypan blue (to assist in visualization) after cryopreservation and thawing, as described in Example 7; Descemet's membrane maintains its transparency and propensity to scroll.

Isolated Descemet's membranes excised from their corneolimbal rings were isolated as described in Example 1, sterilized using antibiotic treatment, frozen at −80° C. for 1 month, and then thawed. After freezing and thawing, the Descemet's membranes maintained their transparency and propensity to scroll. An exemplary sample, stained with Trypan blue (to assist with visibility), is shown in FIG. 10.

Example 8A

This example describes an exemplary method for isolating limbal stem cells from a corneolimbal ring for culture on Descemet's membrane.

Figure 11A:
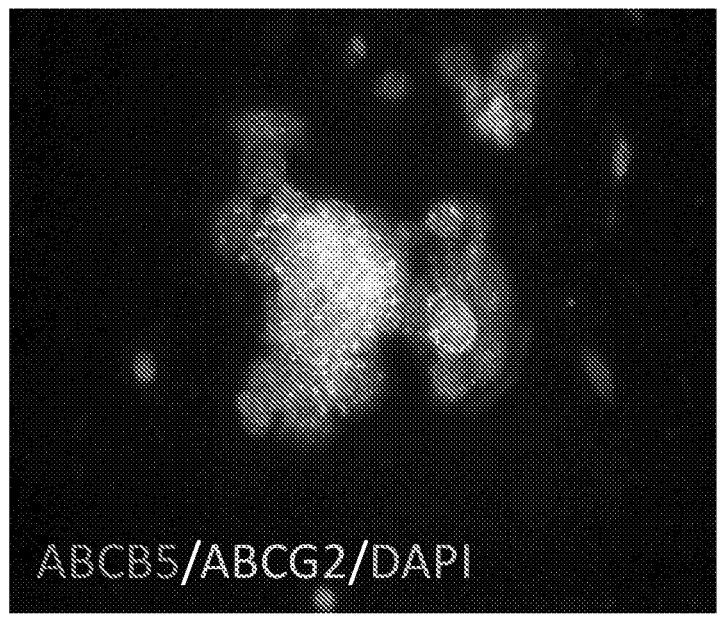
FIG. 11A shows limbal stem cells were released from limbal tissues by collagenase digestion and then immunostained with various limbal stem cell markers and DAPI, as described in Example 8A. Magnification: 40×.

A corneolimbal ring was treated with collagenase to release the basal limbal stem cells, as per previously published protocols (Chen, et al., *Tissue Eng Part C Methods*. 2011; 17:537-548), and resuspended in serum-free medium with bovine pituitary extracts, growth supplement with recombinant components, or chemically defined supplements. After resuspension of the limbal stem cells, the cells were immunostained with limbal stem cell markers (ΔNp63α and ABCG2) and counterstained for nuclei (DAPI), as described in FIG. 4F. Results are shown in FIG. 11A.

These enzymatically isolated limbal stem cells may be further enriched by flow cytometry and seeded onto Descemet's membrane.

After seeding on Descemet's membrane, the cultures can be maintained in (a) growth medium containing human autologous serum, fetal bovine serum, human platelet lysates, or (b) serum-free medium with bovine pituitary extracts, growth supplement with recombinant components or chemically defined supplements.

Example 8B

This example describes an exemplary method for isolating limbal stem cells from a corneolimbal ring for culture on Descemet's membrane.

Figure 11B:
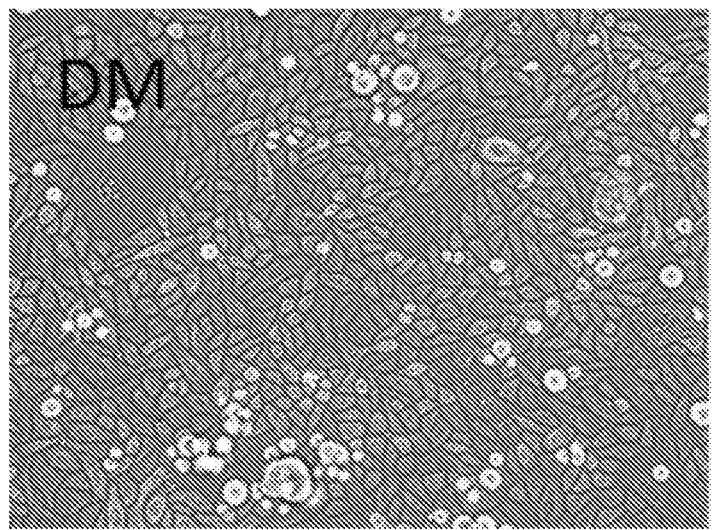
FIG. 11B shows human limbal stem cells that were cultured from limbal explants, then trypsinized and reseeded from cell suspension onto Descemet's membrane, as described in Example 8B. Magnification: 10×.

Limbal explants were prepared by trephining out the central corneal button, then cutting the limbal ring into 12 to 16 small limbal explant fragments. Limbal explant fragments were cultured on tissue culture plastic using serum-free medium with bovine pituitary extracts, growth supplement with recombinant components, or chemically defined supplements. The explants were cultured for 7 to 10 days at 37° C. and 5% $CO_2$, until limbal stem cell outgrowth from the limbal explants was near confluence on the tissue culture plastic. The limbal stem cells were then trypsinized into cell suspension (see Sharifi, et al., *Biocell*. 2010; 34:53-55). Cells were then seeded from suspension onto Descemet's membrane at approximately 20% confluency and allowed to grow for up to 4 to 7 days (resulting in a total period of culture of 14 days). An exemplary image of the resulting Descemet's membrane is shown in FIG. 11B.

Example 9A

Limbal stem cells cultured on tissue culture plastic and Descemet's membrane using different culture conditions were compared for expression of limbal stem cell markers to demonstrate the efficacy of using Descemet's membrane as a culture substrate for limbal stem cells. In the first culture condition, limbal explants were cultured on tissue culture plastic (TCP) using fetal bovine serum (FBS)-supplemented media. In the second culture condition, Descemet's membrane was isolated from the corneoscleral ring as described in Example 1. Limbal explants were then cultured on tissue the isolated Descemet's membrane using fetal bovine serum (FBS)-supplemented media. In the third culture condition, Descemet's membrane was isolated from the corneoscleral ring as described in Example 2, where the limbal stem cells in the intact limbus were exposed to Descemet's membrane and cultured directly onto Descemet's membrane from the intact limbus.

Cultures were then evaluated for outgrowth from limbal explant fragments using inverted light microscopy. One sample for each culture condition that grew to confluence was further characterized with immunohistochemistry. Cultures were immunostained for putative limbal stem cell (LSC) markers: ΔNp63α (nuclear) and ABCG2 (membrane-associated). Cells were then manually counted by two independent reviewers and compared for ΔNp63α and ABCG2 against DAPI nuclear counterstain.

As shown in FIG. 12A, limbal stem cells cultured from limbal explants demonstrated greater stemness, as measured by co-localized expression of putative limbal stem cell markers (ABCG2, ΔNp63α), when cultured on Descemet's membrane (DM) compared to tissue culture plastic (TCP). Furthermore, limbal stem cells cultured from intact limbus demonstrated greater stemness, as measured by co-localized expression of putative limbal stem cell markers (ABCG2, ΔNp63α), in comparison to limbal stem cells cultured from limbal explants.

Example 9B

Limbal stem cells cultured on human amniotic membrane and Descemet's membrane were compared for expression of limbal stem cell markers to demonstrate the efficacy of using Descemet's membrane as a culture substrate for limbal stem cells. Limbal stem cells were trypsinized from limbal explant cultures and suspended in serum free media with bovine pituitary extracts, growth supplement with recombinant components, or chemically defined supplements, as described in Example 8B. Limbal stem cells in suspension were then seeded on human amniotic membrane (HAM) or Descemet's membrane (DM) and maintained in culture at 37° C. and 5% $CO_2$ for 4 to 7 days.

Cultures were then immunostained for putative limbal stem cell (LSC) markers: $\Delta Np63\alpha$ (nuclear) and ABCG2 (membrane-associated). Cells were then manually counted by two independent reviewers and compared for $\Delta Np63\alpha$ and ABCG2 against DAPI nuclear counterstain.

As shown in FIG. 12B, limbal stem cells cultured from cell suspension demonstrated greater stemness, as measured by expression of putative limbal stem cell markers (ABCG2, $\Delta Np63\alpha$), when cultured on Descemet's membrane compared to human amniotic membrane (HAM).

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method comprising:
   removing endothelium from a Descemet's membrane of a cornea to provide a decellularized Descemet's membrane;
   separating the decellularized Descemet's membrane from the stroma of the cornea to obtain an isolated Descemet's membrane;
   adding epithelial cells to the isolated Descemet's membrane in vitro, wherein the epithelial cells are corneal epithelial cells or limbal epithelial cells; and
   culturing the epithelial cells in culture medium that promotes proliferation of the epithelial cells on the anterior surface of the isolated Descemet's membrane.

2. The method of claim 1, wherein the cornea comprises a cadaveric cornea.

3. The method of claim 1, wherein the cornea is human or porcine.

4. The method of claim 1, wherein removing endothelium from a Descemet's membrane comprises at least one of mechanical, enzymatic, or chemical decellularization.

5. The method of claim 1, wherein separating the decellularized Descemet's membrane from the stroma of the cornea comprises injecting fluid or air or both into the cornea.

6. The method of claim 1, the method further comprising using the isolated Descemet's membrane as a cell culture substrate.

7. The method of claim 6, wherein the method comprises using the isolated Descemet's membrane as a cell culture substrate to support proliferation of a limbal stem cell.

8. The method of claim 7, wherein the limbal stem cell adheres to the isolated Descemet's membrane.

9. The method of claim 1, wherein adding the epithelial cells to the isolated Descemet's membrane in vitro comprises adding a limbal explant to the isolated Descemet's membrane in vitro.

10. The method of claim 9, wherein the limbal explant comprises at least a portion of a corneolimbal ring, and wherein the limbal explant is cultured under conditions that allow outgrowth of limbal stem cells from the corneolimbal ring onto the isolated Descemet's membrane.

11. The method of claim 1, wherein adding the epithelial cells to the isolated Descemet's membrane in vitro comprises exposing the isolated Descemet's membrane to a corneolimbal ring in vitro.

12. The method of claim 1, wherein the cell culture medium promotes limbal stem cell growth and/or maintains limbal stem cell pluripotency.

13. The method of claim 1, wherein the method comprises incubating the isolated Descemet's membrane and a limbal stem cell in the cell culture medium at a temperature in a range of 32° C. to 38° C.

14. The method of claim 1, wherein the method further comprises transplanting the isolated Descemet's membrane to an ocular surface of a patient in need thereof.

15. The method of claim 14, wherein the patient exhibits at least one of a partial limbal stem cell deficiency, a total limbal stem cell deficiency, a persistent epithelial defect, an epithelial erosion, a corneal ulcer, a corneal melt, or an ocular surface disease.

16. The method of claim 14, wherein the patient exhibits at least one of an ocular surface trauma, a recurrent erosion, a corneal melt, or a sterile corneal ulcer.

17. The method of claim 1, wherein at least one step is performed in vitro.

18. The method of claim 1, wherein cells proliferate on the anterior surface of the isolated Descemet's membrane in vitro.

19. A method comprising:
   removing endothelium from a Descemet's membrane of a cornea to provide a decellularized Descemet's membrane;
   separating the decellularized Descemet's membrane from the stroma of the cornea to obtain an isolated Descemet's membrane; and
   preparing the isolated Descemet's membrane for transplantation to a subject; and
   transplanting the isolated Descemet's membrane to an ocular surface of a patient in need thereof, wherein the patient exhibits at least one of a partial limbal stem cell deficiency, a total limbal stem cell deficiency, an ocular surface trauma, a persistent epithelial defect, an epithelial erosion, a recurrent erosion, a corneal ulcer, a corneal melt, or an ocular surface disease.

20. The method of claim 19, wherein the cornea comprises a cadaveric cornea.

21. The method of claim 19, wherein the cornea is human or porcine.

22. The method of claim 19, wherein removing endothelium from a Descemet's membrane comprises at least one of mechanical, enzymatic, or chemical decellularization.

23. The method of claim 19, wherein separating the decellularized Descemet's membrane from the stroma of the cornea comprises injecting fluid or air or both into the cornea.

24. The method of claim 19, wherein the method further comprises exposing the isolated Descemet's membrane to an epithelial cell, wherein the epithelial cell is a limbal stem cell or a corneal epithelial cell.

25. The method of claim 24, wherein exposing the isolated Descemet's membrane to the epithelial cell comprises exposing the isolated Descemet's membrane to at least a portion of a corneolimbal ring.

* * * * *